(12) United States Patent
Roine et al.

(10) Patent No.: US 12,061,136 B2
(45) Date of Patent: Aug. 13, 2024

(54) METHOD AND APPARATUS FOR ANALYZING BIOLOGICAL SAMPLES

(71) Applicant: Olfactomics Oy, Tampere (FI)

(72) Inventors: Antti Roine, Tampere (FI); Markus Karjalainen, Tampere (FI); Niku Oksala, Tampere (FI); Anton Kontunen, Tampere (FI); Sampo Saari, Lempäälä (FI)

(73) Assignee: Olfactomics Oy, Tampere (FI)

( * ) Notice: Subject to any disclaimer, the term of this patent is extended or adjusted under 35 U.S.C. 154(b) by 862 days.

(21) Appl. No.: 16/500,054

(22) PCT Filed: Apr. 6, 2018

(86) PCT No.: PCT/FI2018/050254
§ 371 (c)(1),
(2) Date: Oct. 1, 2019

(87) PCT Pub. No.: WO2018/185378
PCT Pub. Date: Oct. 11, 2018

(65) Prior Publication Data
US 2021/0131921 A1    May 6, 2021

(30) Foreign Application Priority Data
Apr. 6, 2017  (FI) ...................... 20175319

(51) Int. Cl.
*G01N 1/22* (2006.01)
*B03C 3/017* (2006.01)
(Continued)

(52) U.S. Cl.
CPC ........... *G01N 1/2202* (2013.01); *B03C 3/017* (2013.01); *B03C 3/41* (2013.01); *B03C 3/47* (2013.01);
(Continued)

(58) Field of Classification Search
CPC ............... G01N 1/2202; G01N 33/497; G01N 2001/028; G01N 2001/045;
(Continued)

(56) References Cited

U.S. PATENT DOCUMENTS

2002/0048818 A1    4/2002  Sakairi et al.
2003/0131727 A1*   7/2003  Fissan ...................... B03C 3/41
                                              96/18
(Continued)

FOREIGN PATENT DOCUMENTS

CN        1646797 A        7/2005
CN      103769299 A        5/2014
(Continued)

OTHER PUBLICATIONS

International Preliminary Report on Patentability, Application No. PCT/FI2018/050254, Date of completion Jul. 4, 2019, 16 pages.
(Continued)

*Primary Examiner* — Michael Maskell
(74) *Attorney, Agent, or Firm* — Ziegler IP Law Group LLC.

(57) ABSTRACT

A measuring apparatus includes
an input to receive an aerosol sample,
a modifier unit to provide a modified sample by removing particles of the aerosol sample, and
a sensor unit to measure a spectral profile by detecting molecules of the gas phase of the modified sample,
wherein the spectral profile is a mobility spectrum or a mass spectrometer spectrum, the modifier unit is arranged to generate a corona discharge, to form charged particles by charging particles of the aerosol sample with the corona discharge, and to provide the modified sample by removing the charged particles with an electric field, the particle removal efficiency of
(Continued)

the modifier unit has a cutoff size to prevent propagation of particles larger than the cutoff size to the sensor unit, and the cutoff size is in the range of 1 nm to 20 nm.

11 Claims, 12 Drawing Sheets

(51) Int. Cl.

| | |
|---|---|
| *B03C 3/41* | (2006.01) |
| *B03C 3/47* | (2006.01) |
| *G01N 27/623* | (2021.01) |
| *G01N 33/497* | (2006.01) |
| *H01J 49/04* | (2006.01) |
| *H01J 49/16* | (2006.01) |
| *G01N 1/02* | (2006.01) |
| *G01N 1/04* | (2006.01) |

(52) U.S. Cl.
CPC ......... *G01N 27/623* (2021.01); *G01N 33/497* (2013.01); *H01J 49/0422* (2013.01); *H01J 49/168* (2013.01); *B03C 2201/06* (2013.01); *B03C 2201/26* (2013.01); *G01N 2001/028* (2013.01); *G01N 2001/045* (2013.01); *G01N 2001/2223* (2013.01)

(58) Field of Classification Search
CPC .......... G01N 2001/2223; G01N 27/622; B03C 3/017; B03C 3/41; B03C 3/47; B03C 2201/06; B03C 2201/26; B03C 3/363; B03C 3/49; H01J 49/0422; H01J 49/168
USPC ....................... 250/281, 282, 288; 73/863.21
See application file for complete search history.

(56) References Cited

U.S. PATENT DOCUMENTS

| | | | | |
|---|---|---|---|---|
| 2010/0127163 | A1 | 5/2010 | Zhdaneev et al. | |
| 2012/0156712 | A1* | 6/2012 | Takats .................. | H01J 49/165<br>435/287.1 |
| 2012/0180659 | A1* | 7/2012 | Laitinen .................... | B03C 3/08<br>96/60 |

FOREIGN PATENT DOCUMENTS

| | | | | |
|---|---|---|---|---|
| CN | 104624023 | A | 5/2015 | |
| EP | 1669562 | A1 | 6/2006 | |
| GB | 1280516 | A | 7/1972 | |
| WO | 03021235 | A1 | 3/2003 | |
| WO | 03074846 | A1 | 9/2003 | |
| WO | 2007012447 | A1 | 2/2007 | |
| WO | 2010003613 | A1 | 1/2010 | |
| WO | WO-2010003613 | A1 * | 1/2010 | ............ B03C 3/016 |
| WO | 2010136887 | A1 | 12/2010 | |
| WO | 2013121094 | A1 | 8/2013 | |
| WO | 2014037617 | A1 | 3/2014 | |
| WO | 2017072396 | A1 | 5/2017 | |

OTHER PUBLICATIONS

Finnish Patent and Registration Office, Application No. 20175319, mailed Oct. 30, 2017, 9 pages.
Written Opinion of the Searching Authority, application No. PCT/FI2018/050254, mailed Jun. 15, 2018, 11 pages.
International Search Report, application No. PCT/FI2018/050254, mailed Jun. 15, 2018, 6 pages.
National Intellectual Property Administration, P.R. China, First Office Action, Application No. 201880023726.3, Mailed Sep. 27, 2021, 8 pages.
European Patent Office, Extended European Search Report, Application No. 18781241.7, Dated Dec. 17, 2020, 10 pages.
Intra et al, "Progress in unipolar corona discharger designs for airborne particle charging: A literature review", Journal of Electrostatics, Elsevier Science Publishers B.V. Amsterdam, NL, vol. 67, No. 4, XP026150997, ISSN: 0304-3886, DOI: 10.1016/ J. Elstat. 2008.12.018, Jul. 1, 2009, pp. 605-615, 11 pages.
Kontunen, Anna, "A System for Intraoperative Cancer Margin Detection by Diathermy Smoke Analysis" Master of Science Thesis, Master's Degree Programme in Biomedical Engineering, Major: Biomeasurements and Bioimaging, XP055757087, Retrieved from URL: https://trepo.tuni.fi/bitstream/hhandle/123456789/25070/kontunen.pdf?sequence=4&isAllowed=y[retrieved on Dec. 7, 2020], Aug. 22, 2017, 79 pages.

* cited by examiner

```
┌─────────────────────────────────────────┐
│  Obtain aerosol sample                  │──── 900
└─────────────────────────────────────────┘
                    ↓
┌─────────────────────────────────────────┐
│  Generate a corona discharge            │──── 910
└─────────────────────────────────────────┘
                    ↓
┌─────────────────────────────────────────┐
│  Charge aerosol particles of the aerosol sample │──── 911
│  by the corona discharge                │
└─────────────────────────────────────────┘
                    ↓
┌─────────────────────────────────────────┐
│  Form modified sample by removing charged particles │──── 920
└─────────────────────────────────────────┘
                    ↓
┌─────────────────────────────────────────┐
│  Provide a measured profile by analyzing the modified sample │──── 930
└─────────────────────────────────────────┘
                    ↓
┌─────────────────────────────────────────┐
│  Compare measured profile with reference data │──── 940
└─────────────────────────────────────────┘
                    ↓
┌─────────────────────────────────────────┐
│  Provide an indication based on the comparison │──── 950
└─────────────────────────────────────────┘
                    ↓
┌─────────────────────────────────────────┐
│  Control operation of an apparatus based on the comparison │──── 960
└─────────────────────────────────────────┘
```

Fig. 6a

METHOD AND APPARATUS FOR ANALYZING BIOLOGICAL SAMPLES

FIELD

Some versions relate to analysis of gaseous components of an aerosol obtained from a biological sample.

BACKGROUND

Gaseous components emitted from a biological sample may be analyzed e.g. by using an ion mobility spectrometer. Particles may contaminate the mobility spectrometer. It is known that particles may be removed from a sample flow by using a fibrous filter or by using a porous membrane filter.

SUMMARY

Some versions relate to an apparatus, which is arranged to analyze an aerosol sample. Some versions relate to a method for analyzing an aerosol sample.

According to an aspect, there is provided an apparatus (200) comprising:
an input (201) to receive an aerosol sample (FG1),
a modifier unit (100) to provide a modified sample (MG1) by removing particles (P1) of the aerosol sample (FG1), and
a sensor unit (SEN1) to measure a spectral profile (PRF) by detecting molecules (VOC1) of the gas phase of the modified sample (MG1), wherein the spectral profile (PRF) is a mobility spectrum or a mass spectrometer spectrum, the modifier unit (100) is arranged to generate a corona discharge (DSR1), to form charged particles (P2) by charging particles (P1) of the aerosol sample (FG1) with the corona discharge (DSR1), and to provide the modified sample (MG1) by removing the charged particles (P2) with an electric field (EF1), the particle removal efficiency (EFF(d)) of the modifier unit (100) has a cutoff size ($d_{CUT}$) to prevent propagation of particles larger than the cutoff size ($d_{CUT}$) to the sensor unit (SEN1), and the cutoff size ($d_{CUT}$) is in the range of 1 nm to 20 nm.

Further aspects are defined in the claims.

The modifier unit may provide a substantially particle-free modified sample flow by using the corona discharge. Using the modifier unit based on the corona discharge may allow reliable particle removal with low pressure loss, and/or with reduced adsorption of volatiles. The modifier unit may provide quick response and a short recovery period for substantially real-time analysis of volatile compounds of an aerosol sample stream.

Using the modifier unit may reduce or prevent contamination caused by aerosol particles. Particles may shorten operating life of one or more components of the measuring apparatus. A need for cleaning and/or replacing the components of the measuring apparatus may be reduced or avoided. Using the modifier unit may allow longer operating time between maintenance operations. Using the modifier unit may even allow substantially maintenance-free operation.

The aerosol sample may be obtained e.g. from a biological material. An aerosol sample obtained from a biological material may comprise bacteria and/or viruses. An issue in analysis of volatile compounds obtained from biological samples may be biological contamination of the sampling system by particles, which carry bacteria and/or viruses. The corona discharge may be arranged to kill bacteria and inactivate the viruses entering the system, thus maintaining sterility in the analytical system. The corona discharge may be arranged to generate chemically active species, e.g. ozone and/or nitrogen oxides. The active species may effectively kill bacteria and may inactivate viruses. Using the modifier unit may facilitate maintaining sterility in the analytical system. Using the modifier unit may facilitate maintaining sterility in one or more other units, which are located downstream the modifier unit.

Particles removed from the sample flow may be carried out of the modifier unit in an auxiliary flow. Consequently, the interaction between the removed particles and the sample flow may be reduced. The modifier unit may be arranged to remove particles from the sample flow such that the removed particles do not capture volatile compounds from the sample flow and/or such that the removed particles do not release volatile compounds to the sample flow. The reduced interaction between the sample flow and the removed particles may allow a fast response to a change of concentration of a volatile compound.

The pressure loss caused by the modifier unit during the operation may be low, e.g. lower than 100 Pa. The pressure loss caused by the modifier unit may be substantially lower than the pressure loss of a porous filter.

As a comparative example, removing substantially all particles by a porous filter may cause high pressure loss, may increase a time delay between sampling and measurement, may degrade temporal resolution of the measurement, and/or may cause adsorption of volatile compounds from the sample to the filter and to the particles trapped to the filter.

BRIEF DESCRIPTION OF THE DRAWINGS

In the following examples, several variations will be described in more detail with reference to the appended drawings, in which FIG. 6a shows, by way of example, method steps for analyzing an aerosol sample.

DETAILED DESCRIPTION

Figure 1A:
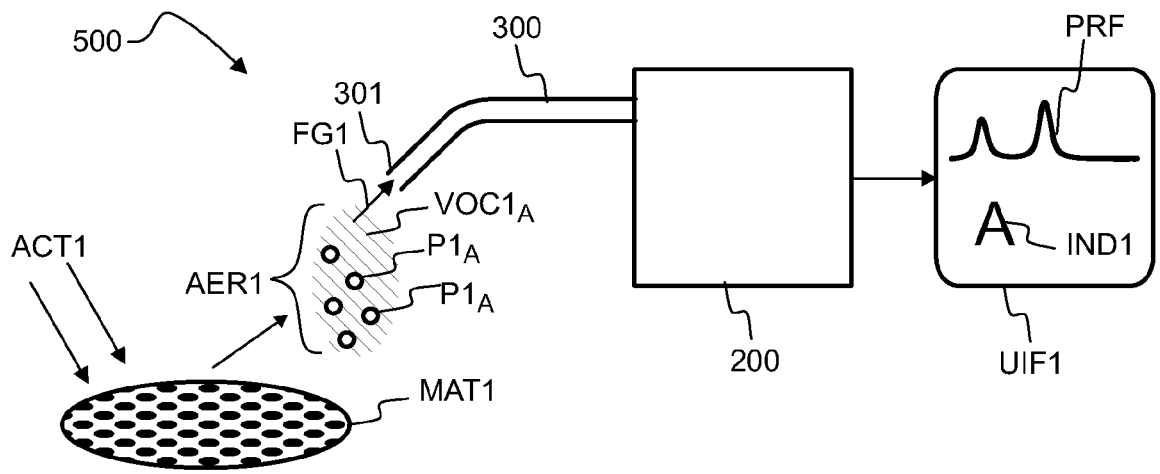
FIG. 1a shows, by way of example, an apparatus for analyzing an aerosol emitted from a first material.

Referring to FIG. 1a, a measuring apparatus 200 may be arranged to analyze an aerosol AER1 obtained from a material MAT1. The material MAT1 may emit the aerosol AER1 e.g. when the material MAT1 is subjected to processing ACT1. The processing ACT1 may comprise e.g. heating the material, and/or exposing the material to a laser beam.

The aerosol AER1 may comprise gaseous components VOC1 and particles P1. The material may emit e.g. gaseous components $VOC1_A$ and particles $P1_A$ when subjected to the processing ACT1. The material MAT1 may be a biological sample. The gaseous components VOC1 may comprise volatile organic compounds obtained from the biological sample.

An aerosol sample FG1 may be obtained via a sampling line 300 to the measuring apparatus 200. A part of the aerosol AER1 may be drawn to the sampling line via an inlet 301. The measuring apparatus 200 may be arranged to provide one or more measured profiles PRF by measuring the gaseous components VOC1 of the aerosol sample FG1. The measured profile PRF1 may be e.g. an ion mobility spectrum determined by a mobility spectrometer. The measured profile PRF1 may be e.g. a mass spectrum determined by a mass spectrometer.

The measuring apparatus 200 may be configured to provide an indicator IND1 indicative of the composition of the aerosol sample FG1. The indicator IND1 may be indicative of the composition of the material MAT1. For example, displaying a symbol (e.g. "A") may indicate that the composition of the gaseous components of the aerosol sample matches with a reference data associated with said symbol ("A").

Figure 1B:
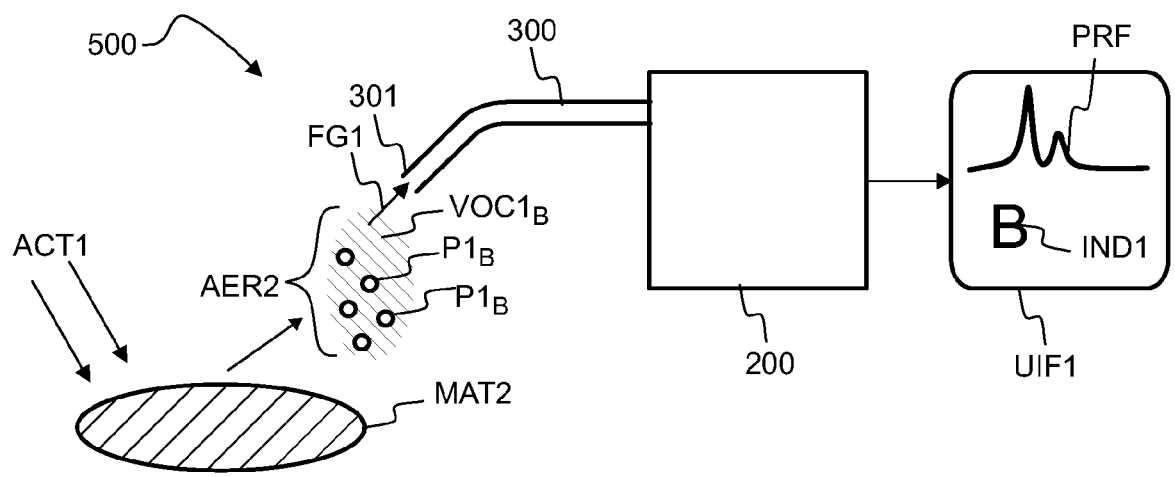
FIG. 1b shows, by way of example, an apparatus for analyzing an aerosol emitted from a second material.

Referring to FIG. 1b, a second material MAT2 may emit an aerosol AER2. The aerosol AER2 may comprise gaseous components $VOC1_B$ and particles $P1_B$. The composition of the second material MAT2 may be different from the composition of the first material MAT1, and the composition of the second aerosol AER2 may be different from the composition of the first aerosol AER1.

The composition of aerosol emitted from a material MAT1 may also depend e.g. on the type of the processing ACT1 and/or on the intensity of the processing ACT1. The measuring apparatus 200 may be configured to provide a signal indicative of an intensity of the processing ACT1.

Figure 2:
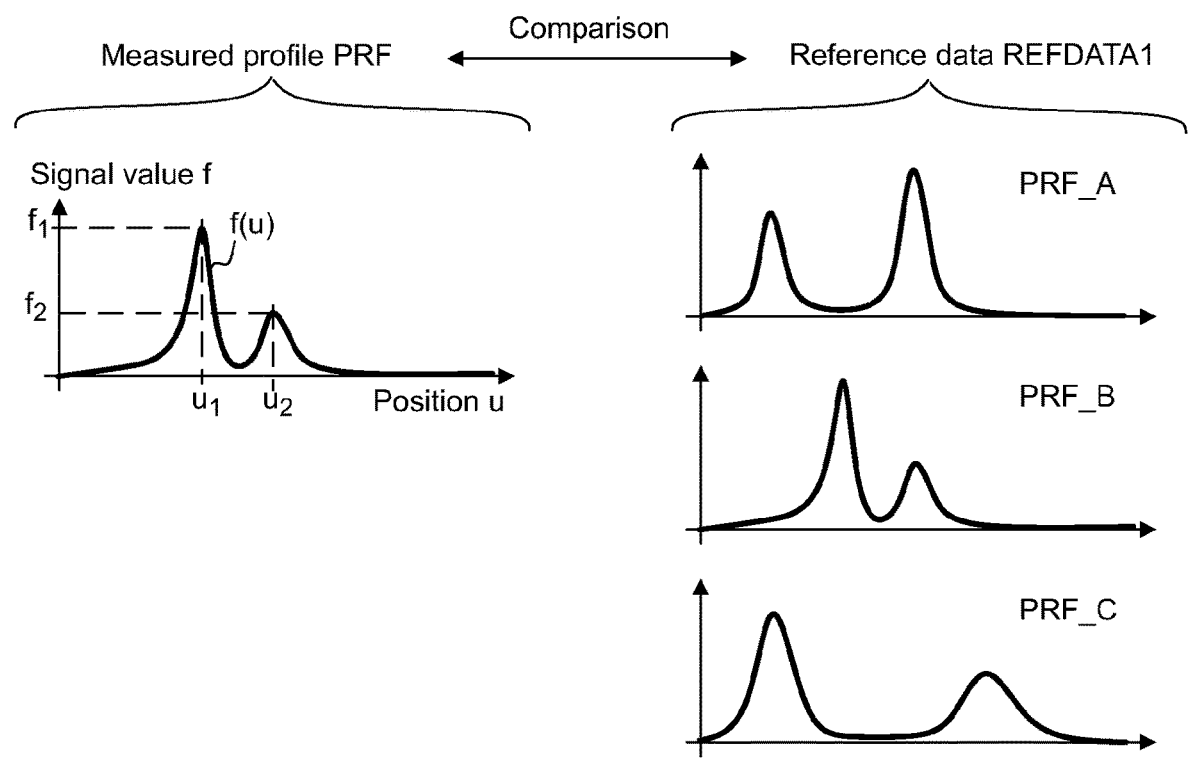
FIG. 2 shows, by way of example, comparing a measured profile with reference data.

Referring to FIG. 2, the measuring apparatus 200 may be arranged to provide one or more measured profiles PRF by analyzing the gaseous components of the sample flow FG1. A measured profile PRF, f(u) may be indicative of the chemical composition of the gaseous phase of sample flow FG1. A profile PRF may specify a signal values as a function of a variable. The variable "u" may be called e.g. as a position or as a spectral position. A measured profile f(u) may comprise a plurality of signal values f expressed as a function of the position u. A measured profile f(u,t) may be indicative of the chemical composition of the gaseous phase of the sample FG1 at a time t. The measured profile f(u,t) may be called e.g. as a characteristic profile of the sample FG1 at a time t.

The apparatus 200 may comprise e.g. a mobility spectrometer. A profile f(u) measured by the apparatus 200 may be a mobility spectrum. The mobility spectrometer may be e.g. an ion mobility spectrometer, a differential mobility spectrometer, and/or a Field Asymmetric Ion Mobility Spectrometer (FAIMS). The apparatus 200 may comprise two or more mobility spectrometers measuring several profiles substantially simultaneously.

The apparatus 200 may comprise e.g. a mass spectrometer. A profile f(u) measured by the apparatus 200 may be a mass spectrum.

The apparatus 200 may be arranged to measure the profiles substantially in real time, or with a short time delay. A first measured profile $f(u,t_1)$ may be determined for a sample FG1 which had a first composition at a time $t_1$. A second measured profile $f(u,t_2)$ may be determined for a sample FG1 which had a second composition at a time $t_2$. A third measured profile $f(u,t_3)$ may be determined for a sample FG1 which had a third composition at a time $t_3$. The composition of the sample FG1 at the time $t_2$ may be different from the composition of the sample FG1 at the time $t_1$. A plurality of measured profiles $f(u,t_1)$, $f(u,t_2)$, $f(u,t_3)$, . . . may be associated with different measurement times $t_1$, $t_2$, $t_3$, . . . .

The apparatus 200 may be configured to compare the measured profile f(u,t) with reference data REFDATA1. The apparatus 200 may be configured to provide an indicator IND1 based on the comparison. The indicator IND1 may e.g. indicate the composition of the sample FG1.

The apparatus 200 may be configured to compare one or more measured profiles (f(u)) with reference data (REFDATA1), and identify one or more substances (e.g. VOC1) and/or materials (e.g. MAT1) based on the comparison. The apparatus may comprise a user interface (UIF1) to provide an indicator (IND1) indicative of an identified substance and/or material.

The indicator IND1 may indicate an estimate for the composition of a material MAT1. The indicator IND1 may indicate a measured composition of a material MAT1. The apparatus 200 may be configured to identify sample material MAT1 based on the comparison.

The reference data REFDATA1 may comprise e.g. three reference profiles PRF_A, PRF_B, PRF_C. A first reference profile PRF_A may be associated with a first material (e.g. MAT1). A second reference profile PRF_B may be associated with a second material (e.g. MAT2). A third reference profile PRF_C may be associated with a third material. The apparatus may be arranged to identify the material by comparing the measured profile with the reference data REFDATA1. For example, the apparatus 200 may be configured to determine whether the sample is obtained from the first material MAT1 or from the second material MAT2. Comparison of the measured profile PRF with the reference data REFDATA1 may indicate e.g. that the measured profile PRF matches with the first reference profile PRF_A, but not with the second reference profile PRF_B.

The reference profiles PRF_A, PRF_B, PRF_C may have been determined previously e.g. by test measurements or by simulation.

The term "substance" may refer e.g. to a solid material, to a liquid substance, and/or to a gaseous substance. A substance may comprise one or more compounds. A substance may consist of a single chemical compound or it may comprise a mixture of different compounds. The term "material" may refer to a tangible substance. A solid tangible material may emit one or more gaseous substances e.g. when the material is subjected to the processing ACT1. A material (e.g. MAT1) may release one or more substances (e.g. volatile compounds VOC1).

Figure 3:
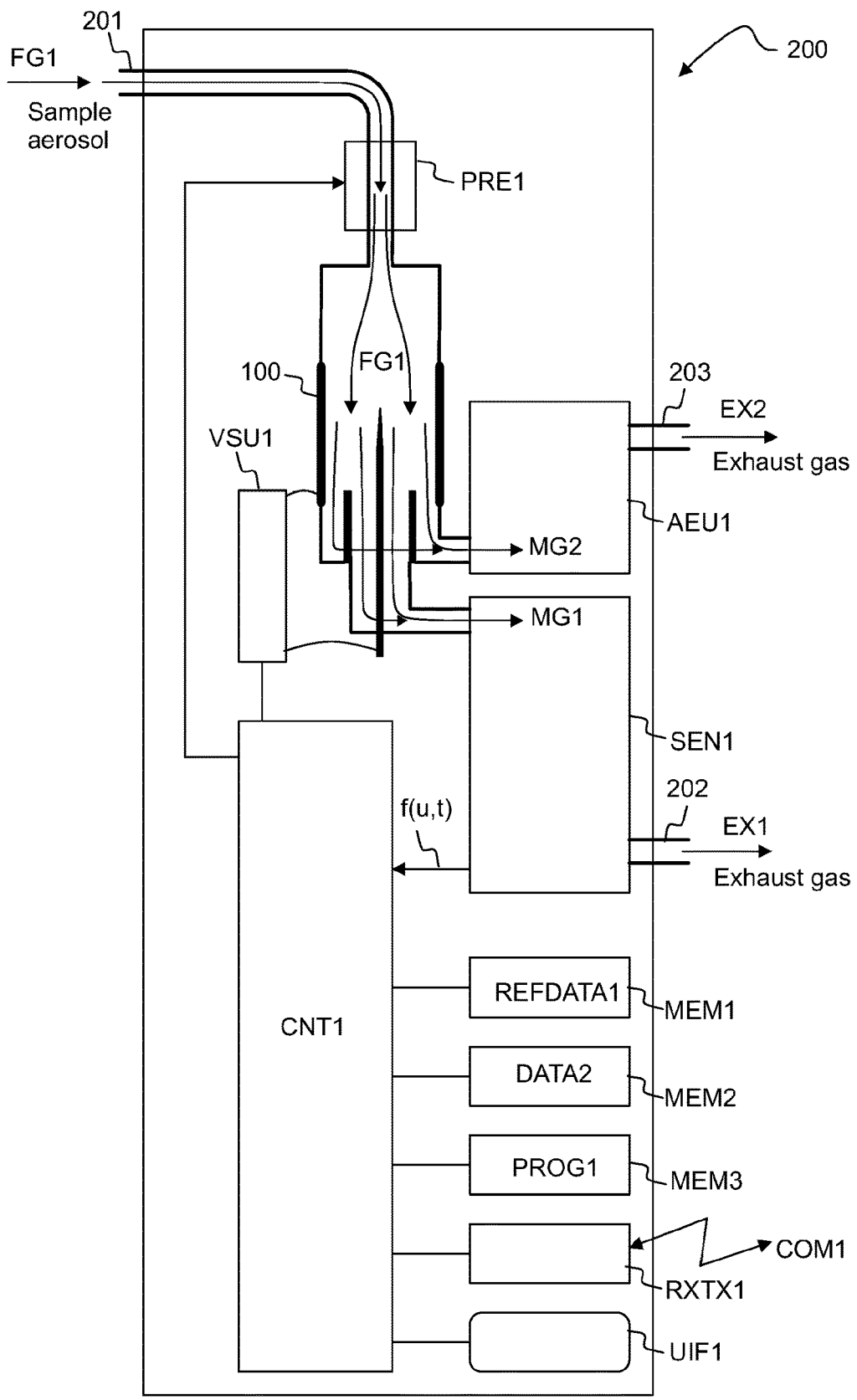
FIG. 3 shows, by way of example, a measuring apparatus for analyzing an aerosol sample.

Referring to FIG. 3, the measuring apparatus 200 may comprise a sample modifier unit 100 to provide a modified sample MG1 by modifying the aerosol sample FG1, and a sensor unit SEN1 to provide one or more measured profiles PRF by measuring the gaseous phase VOC1 of the modified sample MG1.

The measuring apparatus 200 may comprise an inlet 201 for receiving an aerosol sample flow FG1. The modifier unit 100 may be arranged to provide a first partial flow MG1 and a second partial flow MG2 by modifying the sample flow FG1. The first partial flow MG1 may be called e.g. as a modified flow or a depleted flow. The second partial flow may be called e.g. as an enriched flow. The particle concentration of the modified flow MG1 may be substantially lower than the particle concentration of the enriched flow MG2. The modified flow MG1 may be substantially particle-free.

The modified flow MG1 may be guided to the sensor unit SEN1. The sensor unit SEN1 may comprise e.g. one or more mobility spectrometers and/or a mass spectrometer for measuring one or more profiles PRF.

The apparatus 200 may comprise a control unit CNT1 for controlling operation of the apparatus 200. The control unit CNT1 may comprise one or more data processors for processing data.

The apparatus 200 may comprise a memory MEM1 for storing reference data REFDATA1. The apparatus 200 may be arranged to compare one or more measured profiles PRF with the reference data REFDATA1. The apparatus 200 may comprise a memory MEM1 for storing measured data DATA2. The measured data DATA2 may comprise e.g. one or more measured profiles PRF and/or one or more values determined from the measured profiles PRF. The measured data DATA2 may be time-stamped. The apparatus 200 may comprise a memory MEM3 for storing program code PROG1.

The apparatus 200 may comprise a user interface UIF1 e.g. for displaying information to a user and/or for receiving user input from the user. The user interface UIF1 may comprise e.g. a display, a touch screen, a keypad, a mouse, a joystick, a control pedal, a microphone, a speaker, a speech recognition unit, and/or virtual display goggles for providing information to the user and/or for receiving user input. The user interface UIF1 may comprise e.g. a handheld input device to receive user input based on detected position of the handheld input device. The position of the input device may be detected e.g. by using gyro sensors, acceleration sensors, RF field sensors, optical sensors, and/or by analysis of images captured by one or more cameras.

The apparatus 200 may comprise a communication unit RXTX1 for sending and/or receiving data. The apparatus 200 may be arranged to communicate e.g. with a user interface UIF1, with a unit 320, 550 of a measurement system 500, with a wireless communications network (e.g. WLAN, WPAN, "Bluetooth"), with a mobile communications network, and/or with the Internet via the communication unit RXTX1. COM1 may denote a communication signal.

The measuring apparatus 200 may comprise at least one processor CNT1, and a memory MEM3 including computer program code PROG1. The memory MEM3 and the computer program code PROG1 may be configured to, with the at least one processor CNT1, cause the apparatus 200 to perform at least the following:
measuring one or more profiles PRF, and
comparing the profiles PRF with reference data REFDATA1.

The apparatus 200 may be configured to control operation of a system 500 based on the comparison. The apparatus 200 may comprise a control unit CNT1 for comparing the measured profile f(u,t) with reference data REFDATA1. The reference data REFDATA1 may comprise e.g. a plurality of reference profiles. Each reference profile may be associated with a different substance and/or material. The apparatus 200 may comprise a memory MEM1 for storing the reference data REFDATA1. Reference data REFDATA1 may be retrieved e.g. from the memory MEM1, when needed. The apparatus 200 may comprise a memory MEM2 for storing the measured profile f(u,t). The apparatus 200 may be configured to record a plurality of measured profiles $f(u,t_1)$, $f(u,t_2)$, $f(u,t_3)$ in the memory MEM2.

The apparatus 200 may also be configured to perform data processing in a distributed manner. For example, comparison of the measured profiles with reference data may be performed by an internet server. For example, reference data REFDATA1 may be retrieved from a database via the Internet.

Gas which has been analyzed and which has been guided through the sensor unit SEN1 may be vented e.g. to a ventilation duct or room as an exhaust flow EX1 via an outlet 202.

The enriched flow MG2 may be treated as a waste stream. The enriched flow MG2 may be optionally filtered and/or sterilized in an exhaust gas processing unit AEU1. The enriched flow MG2 may be vented e.g. to a ventilation duct or room as an exhaust flow EX2 via an outlet 203.

The apparatus 200 may comprise a voltage supply unit VSU1. The voltage supply unit VSU1 may provide one or more operating voltages for the modifier unit 100.

The measuring apparatus 200 may optionally comprise a pre-treatment unit PRE1. The pre-treatment unit PRE1 may be arranged e.g. to change temperature of the aerosol flow FG1. The pre-treatment unit PRE1 may e.g. increase the temperature of the aerosol flow FG1. The pre-treatment unit PRE1 may e.g. change humidity of the aerosol flow FG1. The pre-treatment unit PRE1 may e.g. dilute the aerosol flow FG1. The pre-treatment unit PRE1 may e.g. add one or more dopants to the aerosol flow FG1.

The apparatus 200 may be arranged to analyze volatile compounds of an aerosol. An aerosol sample may be obtained from a solid sample MAT1 e.g. by headspace analysis or by facilitating the release of volatiles e.g. by a processing ACT1. The processing ACT1 may include e.g. heating, pyrolysis, electrocautery, or laser processing. For liquid samples, heating and or pH modulation may be used. The aerosol may be guided to the measuring apparatus 200 e.g. via a sampling line 300. A carrier gas may be used to facilitate guiding of the aerosol sample FG1 to the measuring apparatus 200. The carrier gas may be e.g. air, purified air, or nitrogen.

The aerosol obtained from a material MAT1, MAT2 may be fed to a pre-treatment unit PRE1, which may be arranged to optimize e.g. sample temperature, humidity and/or dilution ratio. One or more dopants may be added to facilitate detection of one or more selected molecules.

One or more operating parameters of the pre-treatment unit PRE1, one or more operating parameters of the modulating unit 100, and/or one or more operating parameters of pump units PU1, PU2 may be adjusted based on sample information and based on data from the sensors in order to achieve optimal analytical conditions.

The sensor unit SEN1 may comprise an ion mobility spectrometer for analyzing the modified sample MG1. The sensor unit SEN1 may comprise e.g. a differential mobility spectrometer or a field asymmetric mobility spectrometer. The sensor unit SEN1 may comprise a mass spectrometer for analyzing the modified sample MG1. A mobility spectrometer and a mass spectrometer may be arranged to operate in parallel or in series. The apparatus may also comprise two or more mobility spectrometers arranged to operate in parallel or in series.

The apparatus 200 may comprise additional sensors to monitor analytical conditions (e.g. temperature, humidity, pressure). The apparatus 200 may be arranged to control operation of the mobility spectrometer and/or mass spectrometer. The apparatus 200 may be arranged to control operation of the mobility spectrometer and/or mass spectrometer based on the measured profiles and based on information obtained from the additional sensors.

Data gathered from sampling, sample modulation and sensors as well as sample information may be stored as data DATA2 in a database, e.g. in a memory MEM2 Collected data may statistically analyzed and compared to previously collected reference data REFDATA1 to identify the sample MAT1 or to classify it to certain group with certain confidence. Each identified sample may be used to improve a statistical model. Data from analyzed samples may be provided for a user e.g. in a selected report form. The measuring system 500 may be configured to employ one or more learning algorithms such as neural networks to improve analytical models as sampling goes on.

Figure 4A:
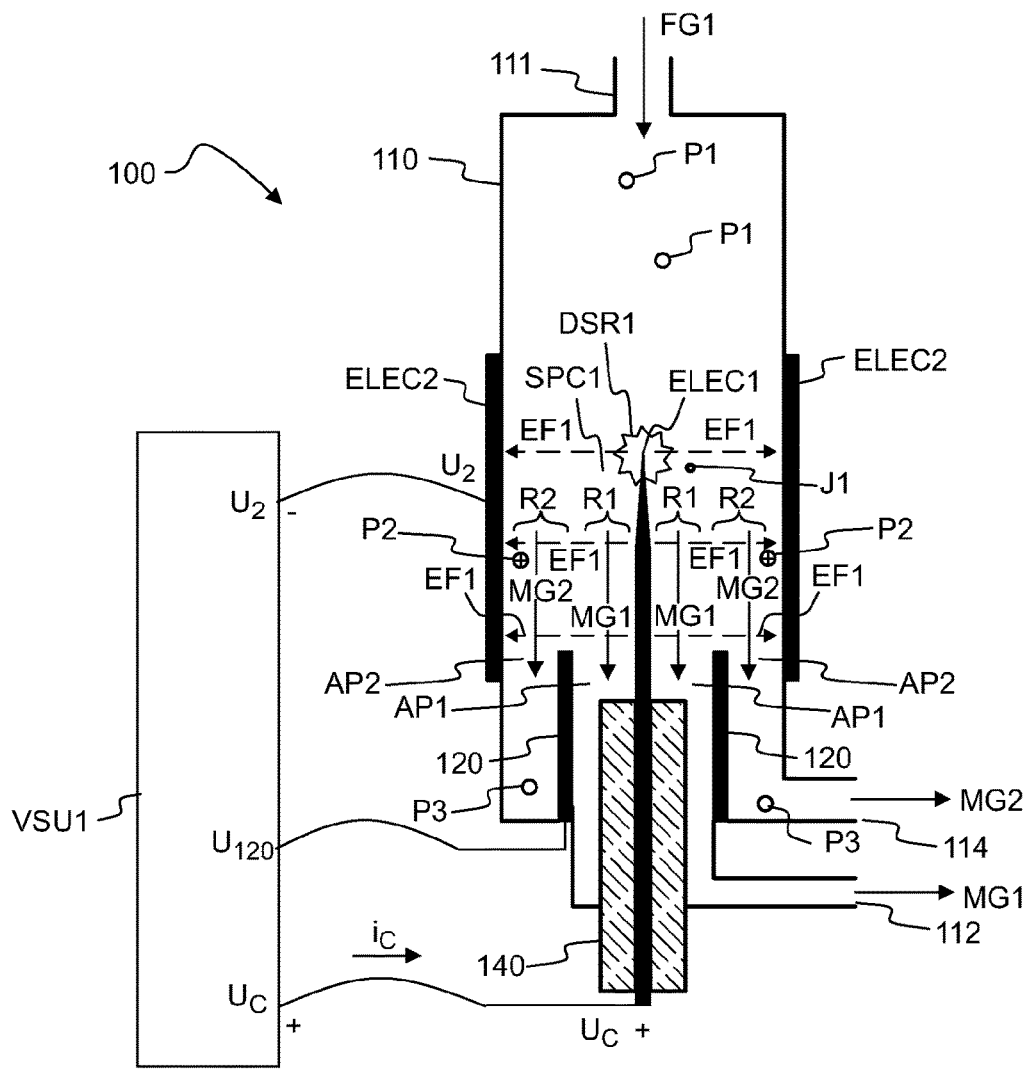
FIG. 4a shows, by way of example, in a cross sectional view, a sample modifier unit.

Referring to FIG. 4*a*, the modifier unit 100 may form charged particles P2 by charging the neutral particles P1. In other words, the modifier unit 100 may be arranged to convert neutral particles P1 of the sample flow FG1 into charged particles P2. The modifier unit 100 may form the charged particles P2 by generating a corona discharge DSR1. The modifier unit 100 may comprise one or more electrodes ELEC1, ELEC2 to generate the corona discharge DSR1. The modifier unit 100 may comprise a corona electrode ELEC1. The corona electrode ELEC1 may be e.g. a needle electrode or a wire electrode. The modifier unit 100 may comprise a counter-electrode ELEC2. A voltage difference $U_C-U_2$ may be applied between the electrodes ELEC1 and ELEC2 to generate an electric field. The electrode ELEC1 may have a voltage $U_C$. The electrode ELEC2 may have a voltage $U_2$. The voltage difference $U_C-U_2$ may be provided e.g. by a voltage supply VSU1. The voltage difference $U_C-U_2$ may be so high that the electric field generated in the vicinity of the corona electrode ELEC1 may locally exceed the breakdown strength of the gaseous phase of the aerosol sample FG1. Consequently, applying the voltage difference $U_C-U_2$ may generate a corona discharge DSR1 in the vicinity of the corona electrode ELEC1. A corona current $i_C$ may be conducted from the corona electrode ELEC1 to the counter-electrode ELEC2. The voltage difference $U_C-U_2$ may be positive or negative. The corona discharge DSR1 may generate ions J1. The ions J1 may be positive and/or negative. The ions J1 may convert neutral particles P1 of the sample flow FG1 into charged particles P2 by charge transfer. The charged particles P2 may carry positive or negative charge.

The sample flow FG1 may be substantially continuously guided to a charging space SPC1 defined by the electrodes ELEC1, ELEC2. The charged particles P2 and the gaseous compounds of the aerosol sample may be guided through the charging space defined by the electrodes ELEC1, ELEC2. The corona discharge DSR1 may generate ions J1. The corona current $i_C$ may be conducted from the corona electrode ELEC1 to the counter-electrode ELEC2 by the ions J1. Particles P1 entering the charging zone between the electrodes ELEC1, ELEC2 may become charged when they receive charge from the ions J1. Particles P1 entering the charging zone between the electrodes ELEC1, ELEC2 may become charged when they transfer charge with the ions J1.

The sample modifier unit 100 may be arranged to provide a modified sample flow MG1, which may be substantially free of particles. The modifier unit 100 may remove the charged particles P2 by using a deflecting electric field EF1.

The modifier unit 100 may comprise two or more field electrodes ELEC1, ELEC2 to generate a particle-deflecting electric field EF1. The electric field EF1 may be arranged to deflect charged particles P2 away from the modified sample flow MG1. The electric field EF1 may be generated e.g. by using the corona electrode and the counter-electrode. However, the modifier unit 100 may also comprise one or more additional deflecting electrodes to generate the deflecting electric field EF1.

Charged particles P2 traveling in the deflecting electric field EF1 may be deflected towards the counter-electrode ELEC2 by said deflecting electric field EF1.

A part of the charged particles P2 may also be deflected towards the corona electrode ELEC1 by the electric field EF1. These particles P2 may be attached to the corona electrode ELEC1 and/or these particles P2 may be carried away by an auxiliary gas flow, after they have been neutralized at the corona electrode ELEC1. The modifier unit 100 may be optionally arranged to provide a third partial flow for removing the particles, which are deflected towards the corona electrode ELEC1.

The aerosol flow FG1 may be converted into a first partial flow MG1 and into a second partial flow MG2 by deflecting the charged particles P2 with the electric field EF1. The direction of the first partial flow MG1 may be substantially parallel with the second partial flow MG2 in the zone defined between the electrodes ELEC1, ELEC2. The electric field EF1 may attract the charged particles P2 towards the electrode ELEC2. The electric field EF1 may deflect the charged particles P2 away from the first partial flow FG1. The electric field EF1 may deflect the charged particles P2 from the first partial flow FG1 to the second partial flow MG2. The electric field EF1 may deflect the charged particles P2 away from the spatial region R1 of the first partial flow FG1 to the spatial region R2 of the second partial flow MG2. The deflected particles may be carried away from the modifier unit 100 with the second partial flow MG2. Deflected charged particles P2 may be neutralized and carried away from the modifier unit 100 with the second partial flow MG2 as neutral particles P3. The modifier unit 100 may comprise a flow divider 120 to separate the first partial flow MG1 from the second partial flow MG2. The flow divider 120 may separate the first partial flow MG1 also from the deflected particles carried by the second partial flow MG2.

The flow divider 120 may be e.g. a substantially cylindrical element positioned between the corona electrode and the counter-electrode. The first partial flow MG1 may be guided from the inter-electrode space via a first aperture AP1. The second partial flow MG2 may be guided from the inter-electrode space via a second aperture AP2. The apertures AP1, AP2 may be annular apertures. The flow divider 120 may partly define the apertures AP1, AP2.

The first partial flow MG1 may be called e.g. as a modified sample flow. The modified sample flow may be substantially free of particles. The modified sample flow MG1 may be guided to the analyzer SEN1 e.g. for analyzing volatile compounds VOC1.

The second partial flow MG2 may be called e.g. as an enriched flow or as a waste flow. The particle concentration of the enriched flow MG2 may be higher than the particle concentration of the aerosol flow FG1 guided to the charging space SPC1. The particle mass concentration of the enriched flow MG2 may be higher than the particle mass concentration of the aerosol flow FG1 guided to the charging space SPC1.

The charged particles P2 may traverse the gas flow towards the counter-electrode ELEC2. The electric field EF1 may separate the charged particles P2 from the first partial flow MG1. The charged particles P2 may become neutral particles P3 when they interact with the electrode ELEC2 or with another conductive surface. The neutralized particles P3 may be carried away from the modifier unit 100 as the enriched flow MG2.

The modifier unit 100 may be arranged to form the first partial flow MG1 and the second partial flow MG2 from the aerosol sample flow FG1 by charging particles P1 of the sample flow FG1 and by deflecting the charged particles P2 with the electric field EF1 from the first partial flow MG1 to the second partial flow MG2. The flow divider 120 may be arranged to separate the first partial flow MG1 from the second partial flow MG2 and from the particles P2, P3 after they have been deflected.

The modifier unit 100 may comprise an inlet 111 to receive the sample flow FG1. The modifier unit 100 may comprise an inlet portion 110 to guide the sample flow FG1 to the charging region. The modifier unit 100 may comprise a first outlet 112 for guiding the modified sample flow MG1 out from the modifier unit 100. The modifier unit 100 may comprise a second outlet 114 for guiding the enriched flow MG2 out from the modifier unit 100.

The corona electrode ELEC1 may be supported e.g. by an electrically insulating element 140. The flow divider element 120 may e.g. surround the corona electrode ELEC1. The flow divider element 120 may separate the first partial flow MG1 from the second partial flow MG2, and the electrodes ELEC1, ELEC2 may be positioned such that the electric field EF1 may separate the charged particles P2 from the first partial flow MG1.

The flow divider 120 may be insulating or electrically conductive. The modifier unit 100 may be arranged to operate such that the flow divider 120 has a floating voltage. Alternatively, the voltage difference between the flow divider 120 and the counter-electrode ELEC2 may be controlled by connecting an electrically conductive flow divider 120 to a controlled voltage $U_{120}$. This may facilitate providing a stable deflecting electric field EF1 in the vicinity of the flow divider 120.

The voltage supply VSU1 may be adjustable. The voltage difference $U_C$–$U_2$ may be adjustable. The measuring apparatus 200 may be arranged to adjust the voltage difference $U_C$–$U_2$.

The voltage supply VSU1 may be arranged to measure or monitor the magnitude of the corona current $i_C$. The magnitude of the current of the electrode ELEC1 and/or ELEC2 may be indicative of particle concentration in the space between the electrodes ELEC1, ELEC2. The measuring apparatus 200 may be configured to determine particle concentration from the measured current $i_C$. The determined particle concentration may be used e.g. as a measured parameter for controlling sampling and/or for data analysis.

A low current $i_C$, a high current $i_C$ and/or large fluctuations of the current $i_C$ may indicate an abnormal condition. The apparatus 200 may be configured to provide an indication if the current $i_C$ of the corona electrode ELEC1 is lower than a first limit value or higher than a second limit value. The apparatus 200 may be configured to provide an alarm if the current is of the corona electrode ELEC1 is outside a predetermined range.

The sample flow FG1 may contain oxygen, and/or nitrogen. The corona discharge DSR1 may also generate active species, e.g. ozone $O_3$, nitrogen oxides $NO_X$ and/or metastable nitrogen ($N_2$). The active species may effectively kill bacteria and/or may inactivate viruses. The active species generated by the corona discharge DSR1 may be mixed with the aerosol flow FG1 in the sample modifier unit 100 in order to kill bacteria and/or in order to inactivate viruses. The active species may interact with the particles P1 and with the charged particles P2 in the modifier unit 100.

Figure 4B:
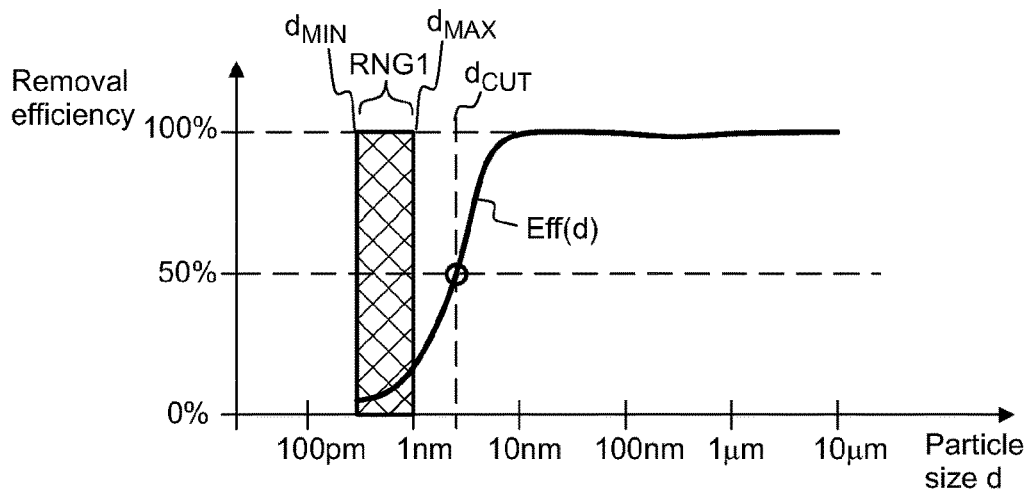
FIG. 4b shows, by way of example, particle removal efficiency of the sample modifier unit as a function of particle size.

FIG. 4b shows, by way of example, particle removal efficiency EFF(d) of the modifier unit 100 as a function of particle size d. The particle removal efficiency EFF(d) of the modifier unit 100 may have a cutoff size $d_{CUT}$. Gaseous molecules (VOC1) smaller than the cutoff size $d_{CUT}$ may pass through the modifier unit 100 to the sensor unit SEN1, wherein the modifier unit 100 may substantially prevent propagation of larger particles (P1) to the sensor unit SEN1.

The sensor unit SEN1 may comprise e.g. a mobility spectrometer or a mass spectrometer. The first partial flow MG1 may be guided from the modifier unit 100 to the spectrometer (MS1). The modifier unit 100 may pass gaseous molecules of the sample FG1 to the spectrometer, while substantially preventing propagation of the larger particles to the spectrometer. The combination of the modifier unit 100 and the spectrometer may provide a fast response for detecting molecules of the gas phase, wherein the modifier unit 100 may effectively prevent or reduce contamination of the spectrometer.

The spectrometer may provide a spectral profile PRF, which represents a size range RNG1 of molecules (VOC1). The size range RNG1 may have a lower size limit $d_{MIN}$ to an upper size limit $d_{MAX}$. The lower limit $d_{MIN}$ may be e.g. smaller than or equal to 300 pm, and the upper limit $d_{MAX}$ may be e.g. in the range of 500 pm to 2 nm. The lower limit $d_{MIN}$ may represent e.g. a water molecule (mass 18 u), and the upper limit $d_{MAX}$ may represent a molecule, whose mass is in the range of 500 u to 5000 u. u denotes the unified atomic mass unit.

The cutoff size $d_{CUT}$ of the modifier unit 100 may be greater than the upper limit $d_{MAX}$ of the measurement range RNG1 of the spectrometer. The cutoff size $d_{CUT}$ may be e.g. in the range of 1 nm to 20 nm, preferably in the range of 2 nm to 10 nm. The particle removal efficiency EFF(d) of the modifier unit 100 at d=100 nm may be e.g. greater than or equal to 99.9%. The particle removal efficiency EFF(d) of the modifier unit may be e.g. greater than or equal to 99.9% in the particle size range from 100 nm to 10 μm.

The cutoff size $d_{CUT}$ may depend on the operating conditions of the modifier unit 100. The particle removal efficiency function EFF(d) may depend e.g. on the strength of the electric field, on the flow rate of the sample flow FG1, on the geometry of the modifier unit 100, on the composition of the particles, on the shape of the particles, on the temperature of the sample flow FG1, and/or on the composition of the gaseous phase of the sample flow FG1. The cutoff size $d_{CUT}$ may be adjusted e.g. by selecting the strength of the electric field, by selecting the flow rates of the flows FG1, MG1, MG2, and/or by selecting the geometry of the modifier unit 100. The cutoff size $d_{CUT}$ may depend on the composition of the particles, on the shape of the particles, on the temperature of the sample flow FG1, and/or on the composition of the gaseous phase of the sample flow FG1.

The particle removal efficiency EFF(d) may increase gradually with increasing particle size d in the vicinity of the cutoff size $d_{CUT}$. A major fraction of gaseous molecules smaller than the cutoff size $d_{CUT}$ may pass through the modifier unit 100 to the first partial flow MG1, wherein a major fraction of particles larger than the cutoff size $d_{CUT}$ may be deflected to the second partial flow MG2. The removal efficiency Eff(d) may attain the value 50% at the cutoff size $d_{CUT}$. The concentration of particles having the size $d_{CUT}$ in the first partial flow MG1 may be equal to 50% of the concentration of particles having the size $d_{CUT}$ in the sample flow FG1. 100% removal efficiency may mean that the concentration of particles having a given size d in the first partial flow MG1 is equal to 0%. 0% removal efficiency may mean that the concentration of particles having a given size d in the first partial flow MG1 is equal to the concentration of particles having said size d in the sample flow FG1.

The corona discharge may generate active species. The active species may interact with the volatile compounds VOC1 and/or with the particles. Interaction of the active species with the volatile compounds and/or with the particles P1 may generate new molecules, which in turn may further modify the molecular size distribution in the first partial flow MG1. The interaction may generate further gaseous molecules, which in turn may be detected by the spectrometer. The interaction of the active species with the volatile compounds VOC1 and/or with the particles may facilitate identification and/or analysis of a material MAT1.

A part of the sample flow FG1 may be guided to the charging space SPC1 via the corona discharge DSR1, e.g. in order to generate active species and/or further gaseous molecules.

Figure 4C:
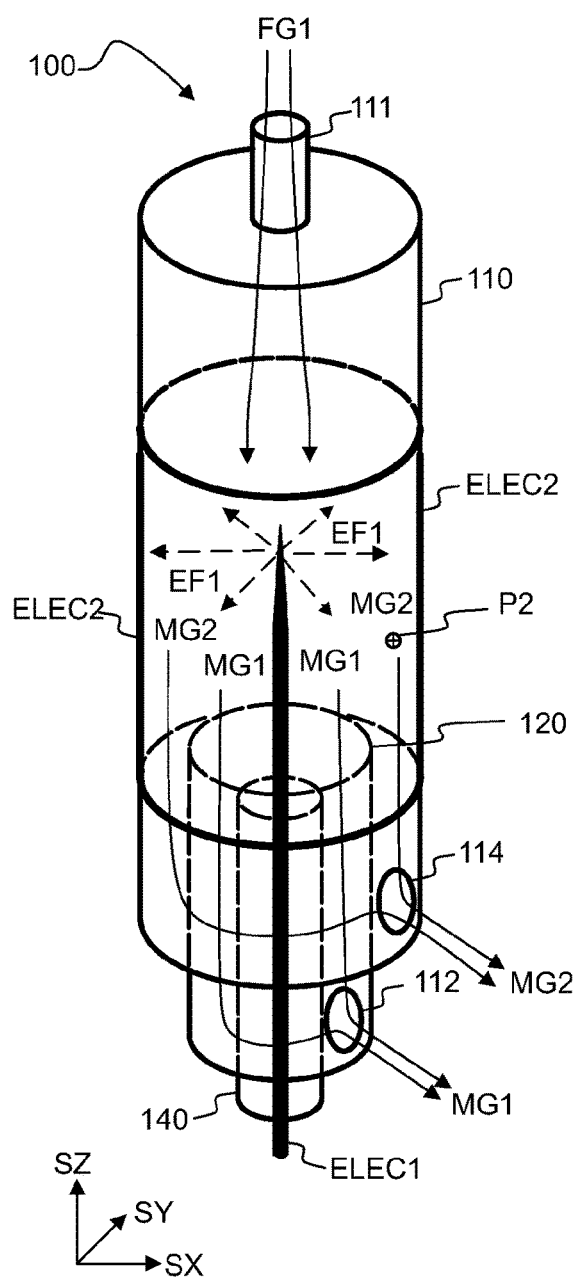
FIG. 4c shows, by way of example, in a three dimensional view, a sample modifier unit.

Referring to FIG. 4c, the spatial region of the first partial flow MG1 may substantially concentrically surround the corona electrode ELEC1, in the volume defined between the electrodes ELEC1, ELEC2. The spatial region of the second partial flow MG2 may substantially concentrically surround the first partial flow MG1, in the volume defined between the electrodes ELEC1, ELEC2.

The counter-electrode ELEC2 may substantially concentrically surround the corona electrode ELEC1. The flow divider element 120 may substantially concentrically surround the corona electrode ELEC1.

The counter-electrode ELEC2 may substantially concentrically surround the corona electrode ELEC1 and the flow divider 120.

SX, SY and SZ denote orthogonal directions.

Figure 4D:
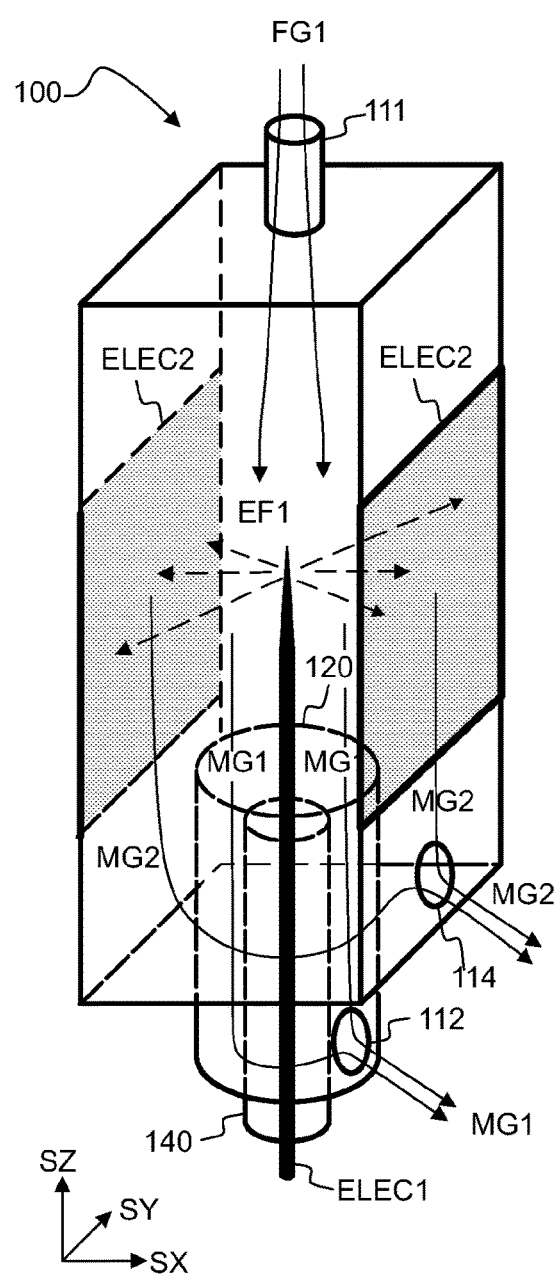
FIG. 4d shows, by way of example, in a three dimensional view, a sample modifier unit.

Referring to FIG. 4d, the cross section of the flow channel defined by the electrode ELEC2 or by electrodes ELEC2 may be e.g. rectangular.

Figure 5A:
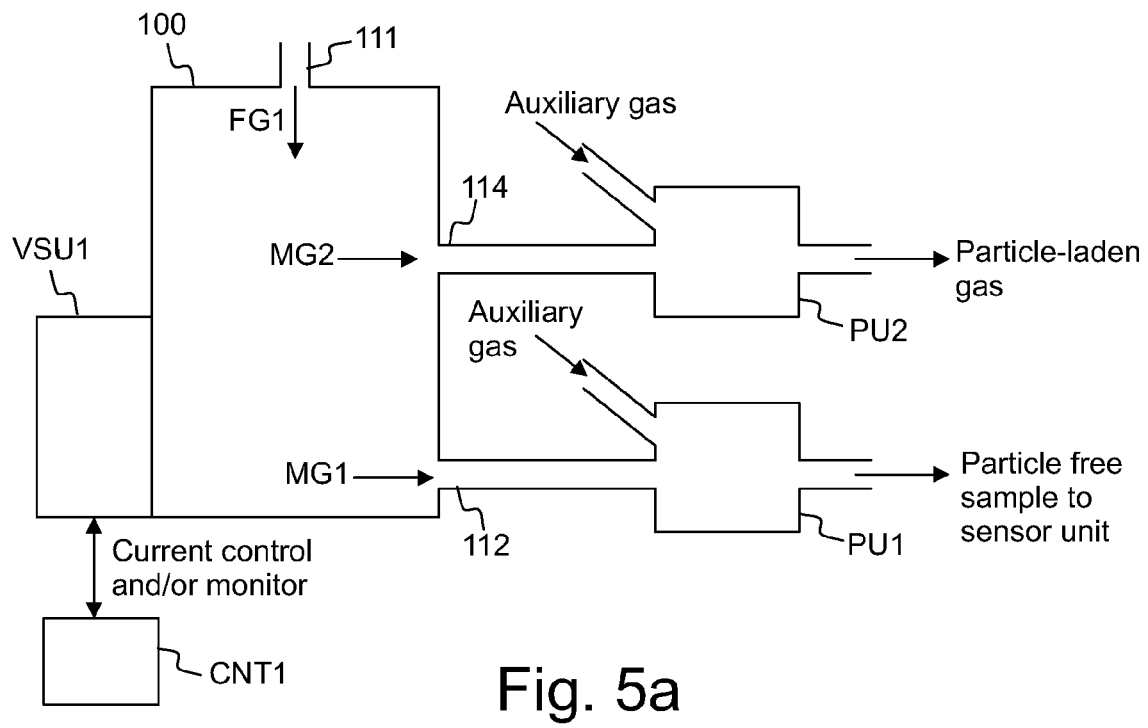
FIG. 5a shows, by way of example, pump units arranged to cause a first partial flow and a second partial flow out of the modifier unit.

Referring to FIG. 5a, the measuring apparatus 200 may comprise one or more pumping units PU1, PU2 for causing the flows FG1, MG1 and MG2. The measuring apparatus 200 may be arranged to control and/or maintain substantially continuous flows FG1, MG1 and MG2. The measuring apparatus 200 may comprise a pumping unit PU1 for drawing the modified sample flow MG1 out from the modifier unit 100. The measuring apparatus 200 may comprise a pumping unit PU2 for drawing the enriched flow MG2 out from the modifier unit 100. A pumping unit PU1, PU2 may be implemented e.g. by an ejector. In particular, the modified sample flow MG1 may be drawn by using a first ejector, and the enriched flow MG2 may be drawn by using a second ejector.

Figure 5B:
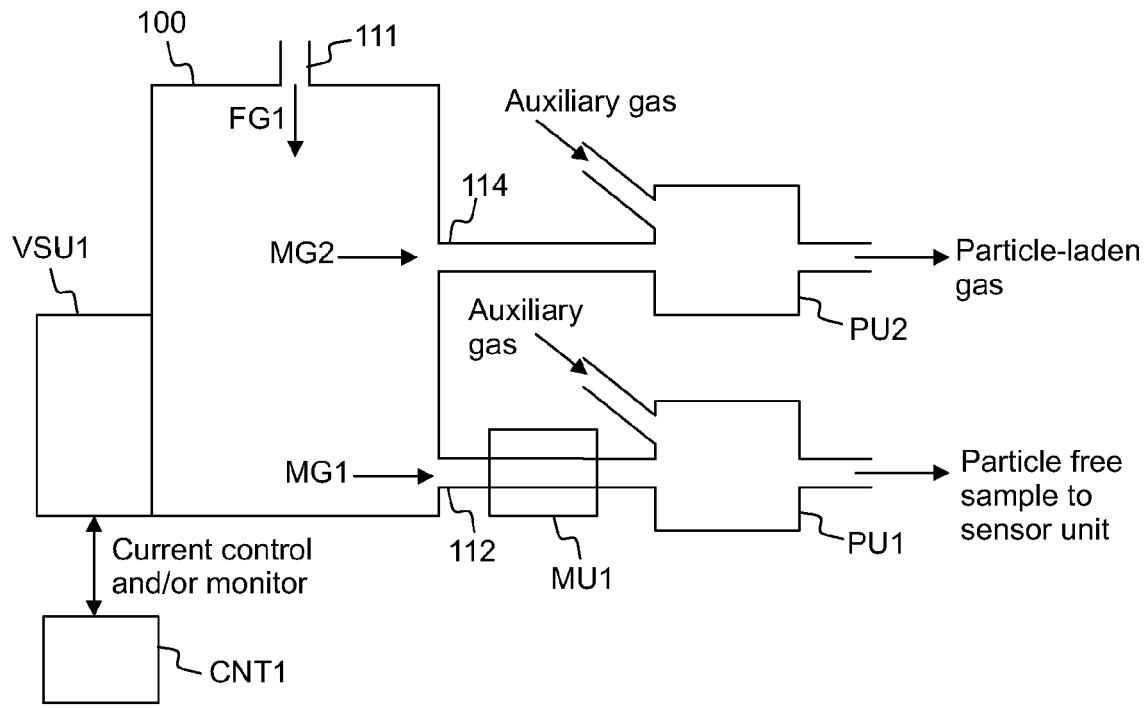
FIG. 5b shows, by way of example, a monitoring unit arranged to monitor the modified sample flow.

Referring to FIG. 5b, the apparatus 200 may comprise a monitoring unit MU1 for monitoring the modified sample flow MG1. The monitoring unit MU1 may comprise e.g. an optical measuring unit for monitoring particle concentration of the modified sample flow MG1. The monitoring unit MU1 may comprise e.g. a temperature probe for monitoring temperature of the modified sample flow MG1. The monitoring unit MU1 may comprise e.g. a humidity probe for monitoring the concentration of water vapor of the modified sample flow MG1. The operation of the modifier unit 100, the operation of the pre-treatment unit PRE1 and/or the operation of the pumping unit(s) may be controlled based on information obtained from the monitoring unit MU1.

FIG. 6a shows, by way of example, method steps for analyzing an aerosol sample obtained from a material. The aerosol sample FG1 may be obtained (step 900). The corona discharge may be generated (step 910), and the particles P1 of the sample may be converted into charged particles P2 (step 911). The modified sample MG1 may be formed by using the electric field EF1 to separate the charged particles P2 from the gas phase of the modified sample MG1 (step 920). One or more profiles PRF may be provided by analyzing the gas phase of the modified sample MG1 (step 930). One or more profiles PRF may be compared with reference data REFDATA1 (step 940). An indicator IND1 may be provided based on the comparison (step 950). The indicator IND1 may indicate e.g. a composition of a material. Operation of an apparatus may be optionally controlled based on the comparison (960).

Figure 6B:
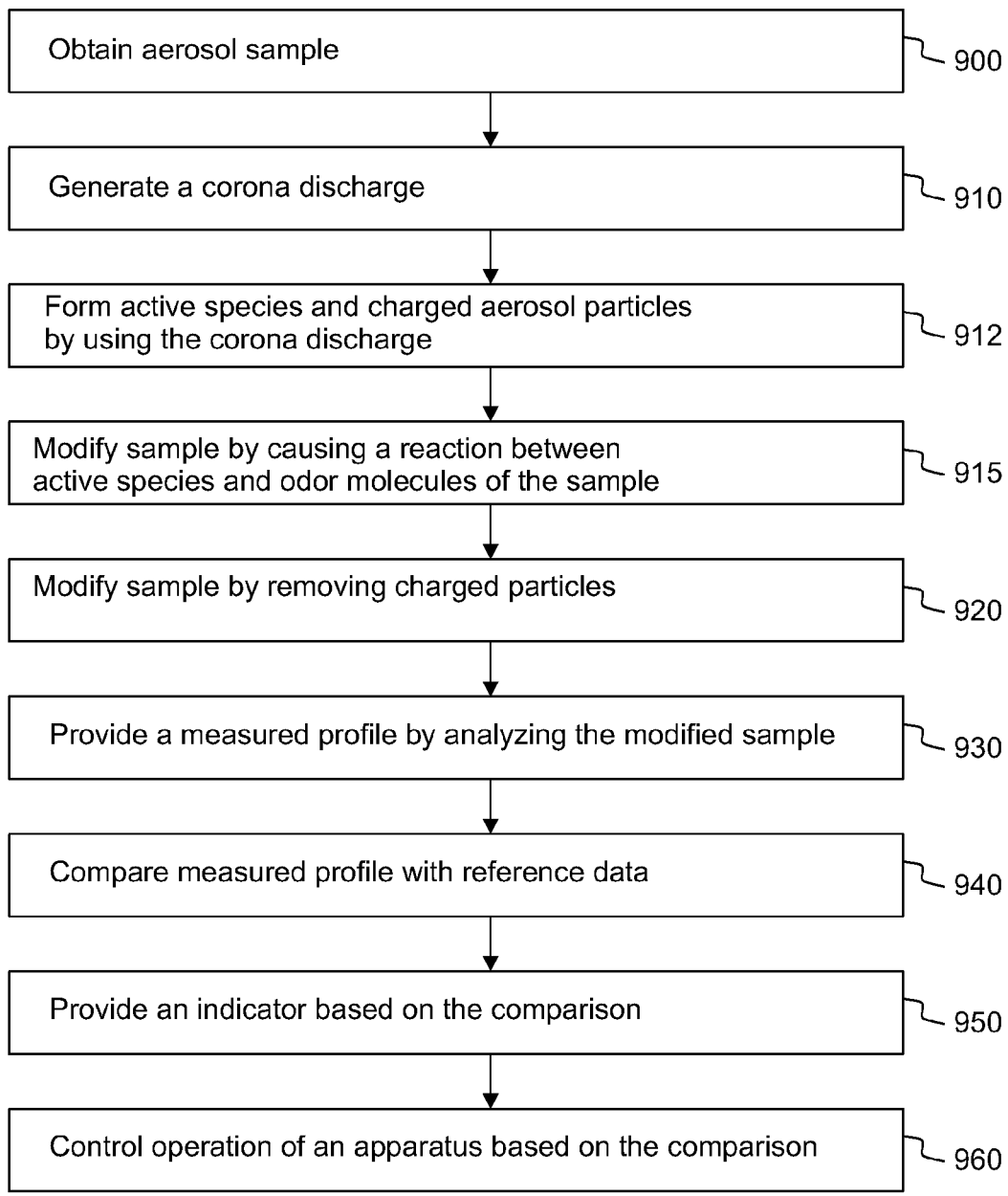
FIG. 6b shows, by way of example, method steps for analyzing an aerosol sample.

FIG. 6b shows, by way of example, method steps for analyzing an aerosol sample obtained from a material. Steps 900, 910, 920, 930, 940, 950, 960 may be performed as discussed above. In addition, the modifier unit 100 may be arranged to generate active species e.g. by guiding at least a part of the sample flow FG1 via the corona discharge DSR1 (step 912). The active species may interact with the gaseous compounds VOC1 and/or with the particles P1, P2 (step 915).

Figure 7:
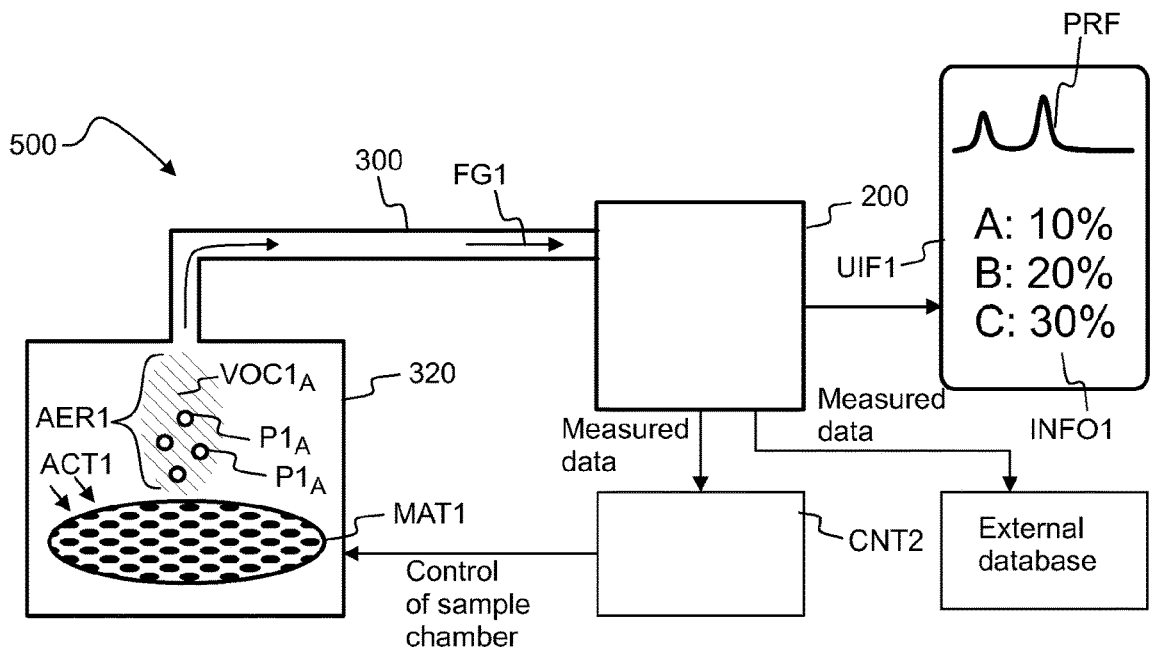
FIG. 7 shows, by way of example, a measuring system, which comprises a sample chamber.

Referring to FIG. 7, a measurement system 500 may comprise a sample chamber 320. Sample material MAT1 may be positioned into the chamber 320. Aerosol AER1 may be obtained from the material MAT1. A sampling line 300 may guide a sample flow FG1 from the chamber 320 to the apparatus 200. The gaseous components VOC1 of the sample flow FG1 may be analyzed by using the apparatus 200. Operation of the measurement system 500 may be controlled based on the measured profiles PRF.

The system 500 may be used e.g. for analyzing a microbiological sample MAT1. The measuring system 500 may be configured to estimate (i.e. determine) a composition of the material MAT1 e.g. in a situation where the sample MAT1 and clinical data are fed to the system 500.

Clinical data concerning the sample may be communicated to the system 500. For example, a user may feed clinical data e.g. by using the user interface UIF1 and/or by using an internet service. The system 500 may be configured to select a relevant subset of the reference data REFDATA1 according to the clinical data, in order to facilitate comparison and/or in order to improve reliability of identifying the components of the sample.

The sample may be associated with an identifier. The identifier may be e.g. a code, an RFID tag or barcode. The system 500 may automatically retrieve relevant clinical data based on the identifier. The clinical data may be retrieved e.g. from an electronic patient database.

The aerosol sample FG1 containing volatile organic compounds may be guided via the sampling line 300 to the apparatus 200. The system 200 may estimate the composition of the sample by analyzing the composition of the gas phase of the modified sample MG1. The system 200 may be configured to estimate the composition of the sample MAT1 by comparing the measured profiles PRF the reference data REFDATA1. The system 200 may be configured to estimate the composition of the sample MAT1 by comparing the measured profiles PRF with a relevant subset of the reference data REFDATA1. The estimated composition may be displayed to the user e.g. as information INFO1. The estimated composition may be stored in a database. The estimated composition may be communicated e.g. to a laboratory management system and/or to an electronic patient record. The estimated composition may be stored e.g. in a memory MEM2. One or more operating parameters of the chamber 320 may be optimized based on one or more measured profiles PRF.

Figure 8:
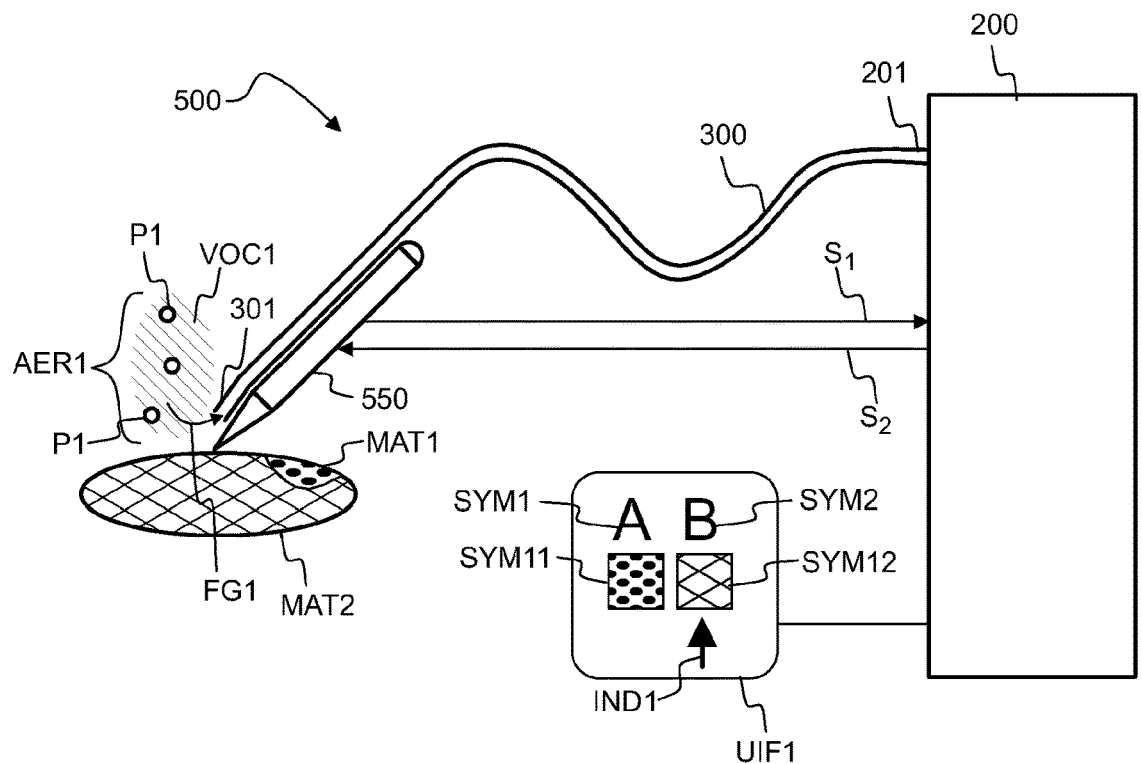
FIG. 8 shows, by way of example, a system, which comprises a surgical instrument.

Referring to FIG. 8, a system 500 may comprise a surgical instrument 550 and the measuring apparatus 200. The instrument 550 may be e.g. an electrosurgical tool. The surgical instrument 550 may be e.g. a diathermy knife. The instrument 550 may be e.g. a laser processing unit. The instrument 550 may be e.g. an ultrasonic cutting instrument.

An electrosurgical instrument, an electrocautery instrument, a laser instrument, a plasma instrument, or an ultrasound cutting instrument may be used to remove and/or treat a tissue MAT1, MAT2 of a patient.

The instrument 550 may be arranged to process tissue MAT1, MAT2. The instrument 550 may cause emission of aerosol AER1 by processing.

The system 500 may comprise the surgical instrument 550 for causing emission of aerosol AER1 from a tissue MAT1 by processing ACT1, and an inlet 301 for sampling the aerosol AER1. The system 500 may comprise a sampling line 300 for guiding the aerosol sample FG1 from the inlet to the measuring apparatus 200. The tissue MAT1, MAT2 may emit an aerosol AER1 during operation of the instrument 550. The system 500 may be arranged to guide an aerosol sample AER1, FG1 from the inlet 301 of the sample line 300 to the apparatus 200 during operation of the surgical instrument 550. The system 500 may be arranged to analyze the aerosol AER1.

Processing the tissue by the instrument 550 may cause emission of an aerosol AER1, which comprises volatile organic compounds and particles P1. The system 500 may be arranged to sample and analyze the aerosol AER1, FG1 emitted during operation of the instrument 550. The system 500 may be arranged to analyze the composition of the gaseous phase of the aerosol AER1, FG1. The system 500 may be arranged to identify the processed material MAT1, MAT2 based on the analysis. The system 500 may be arranged to identify the processed material MAT1, MAT2 substantially in real time, or with a short time delay.

The system 500 may be arranged to receive the aerosol sample AER1, FG1 emitted from a sample material MAT1, to form the modified sample MG1 from the aerosol AER1, to provide one or more measured profiles f(u) by analyzing the modified sample MG1, and to provide one or more indicators (IND1) by comparing the measured profiles f(u) with reference data REFDATA1.

The system 500 may be arranged to compare one or more measured profiles f(u) with reference data REFDATA1, to determine a type of material based on the comparison, and to provide an indication IND1 indicative of the determined type of material.

Information about the determined composition of the material may be displayed by displaying the indicator IND1. The indicator IND1 may be displayer e.g. together with one or more symbols SYM1, SYM2, SYM11, SYM12. Displaying a limited number of symbols may also indicate the number of different materials of the selected subset of the reference data.

The system 500 may be arranged to indicate e.g. whether a measured profile PRF of the gaseous phase VOC1 of the sampled aerosol FG1 matches with a first reference profile (e.g. PRF_A) or with a second reference profile (e.g. PRF_B). The system 500 may be arranged to indicate e.g. whether the instrument 550 is processing a material MAT1 of a first type or a material MAT2 of a second type. The system 500 may be arranged to indicate a similarity between a measured profile PRF and a reference profile (PRF_A, PRF_B).

The system 500 may be arranged to indicate whether the instrument 550 is processing a material MAT1 of a first type or not. The system 500 may be arranged to indicate whether a measured profile PRF matches with a reference profile (e.g. PRF_A) or not.

The system 500 may be arranged to indicate, based on analysis of the aerosol AER1, whether the instrument 550 is processing a first material MAT1 or a second material MAT2. The first material MAT1 may refer to e.g. to a tumor, and the second material MAT2 may refer to normal tissue. The system 500 may be arranged to indicate e.g. to a surgeon whether the instrument 550 is cutting e.g. a tumor MAT1 or normal tissue MAT2.

The system 500 may be arranged to indicate whether the measured profile PRF of the gas phase of the aerosol AER1 matches with a reference profile (e.g. PRF_A) of a first tissue or with a reference profile of a second tissue (e.g. PRF_B). The first tissue may be associated e.g. with an identifier "abnormal", and the second tissue may be associated e.g. with an identifier "normal".

The first material MAT1 may also be e.g. normal muscle tissue, and the second material MAT2 may be e.g. normal fat tissue. The system 500 may be arranged to indicate whether the instrument 550 appears to be cutting muscle tissue or fat tissue. The system 500 may be arranged to provide an indication IND1, which indicates whether the measured profile PRF of the gas phase of the aerosol AER1 matches with a reference profile of fat tissue or with a reference profile of muscle tissue.

In the beginning of an operation, a relevant subset of the reference data REFDATA1 may be selected e.g. based on available clinical data (e.g. target organ, and/or tumor type). Selecting the relevant subset may improve reliability of the identification.

A surgeon may use the instrument 550 to dissect the tissue MAT1 and/or MAT2 and may feed the observed landscape from the surgical theatre (e.g. a two-button system normal-suspicious). Operation of the instrument 550 may cause emission of volatiles VOC1 and particles P1. Every time the instrument 550 is used in a suspicious-mode, the sample may be fed to the measuring apparatus 200. Operating current of the instrument 550 and/or other operating parameters of the instrument 550 may be automatically fed to the system 500 as well. The system 500 may analyze the sample flow FG1 and compare the measured profiles PRF with the relevant reference data REFDATA1. The system 500 may estimate the composition of the aerosol sample AER1, FG1 based on the comparison. The system 500 may determine the type of the processed material substantially in real time, by analyzing the sample FG1. The system 500 may identify the processed material substantially in real time. An indicator for the material may be provided to the surgeon e.g. by an audio, visual and/or haptic signal. The system 500 may be configured to provide additional information based on the measured profile PRF. For example, the system 500 may be configured to provide an advice for re-sampling in a situation where statistical analysis of the profiles indicates that the measurement result is not reliable. For example, the system 500 may be configured to provide an advice for modifying the sampling environment (e.g. cleaning target area from blood in a situation where the concentration of volatile compounds originating from blood exceeds a predetermined level).

The system 500 may comprise the sampling line 300 for guiding the aerosol sample FG1 from via the inlet 301 to the apparatus 200. The inlet 301 may be positioned in the vicinity of the instrument 550 so as to sample the aerosol AER1. The distance between the inlet 301 and an end of the instrument 550 may be e.g. smaller than or equal to 0.5 m, advantageously smaller than 0.1 m, and preferably smaller than 0.02 m. The inlet 301 may be e.g. attached to the instrument 550.

The instrument 550 may be optionally arranged to provide a monitor signal $S_1$ to the apparatus 200. The monitor signal $S_1$ may be indicative of the proximity of the material MAT1, the impedance of the material MAT1 and/or a color of the material MAT1. The material MAT1 may have a color in the infrared, visible and/or ultraviolet region of light. The apparatus 200 may be optionally arranged to provide a control signal $S_2$ for controlling operation of the instrument 550.

The reference data REFDATA1 may comprise data (PRF_A, PRF_B, PRF_C) associated with different tissues of human or animal body. The reference data REFDATA1 may comprise one or more reference profiles (PRF_A, PRF_B, PRF_C) associated with tissues of human or animal body. The reference data REFDATA1 may comprise e.g. a first reference profile (PRF_A) associated with a first type of tissue, the reference data REFDATA1 may comprise a second reference profile (PRF_B) associated with a second type of tissue, and the reference data REFDATA1 may comprise a third reference profile (PRF_C) associated with a third type of tissue, Processing of a tissue may be associated with a surgical and/or therapeutic effect. However, a tissue may be processed also without carrying out a method for treatment of the human or animal body by surgery, and/or without carrying out a method for treatment of the human or animal body by therapy. For example, a tissue may be heated and/or exposed to a laser beam without causing a surgical and/or therapeutic effect. A tissue may also emit small amounts of gaseous components without any processing.

Aerosol AER1 emitted from a tissue may be received, modified, and analyzed without carrying out a method for treatment of the human or animal body by surgery, without carrying out a method for treatment of the human or animal body by therapy, and/or without carrying out a diagnostic method practiced on the human or animal body.

Figure 9:
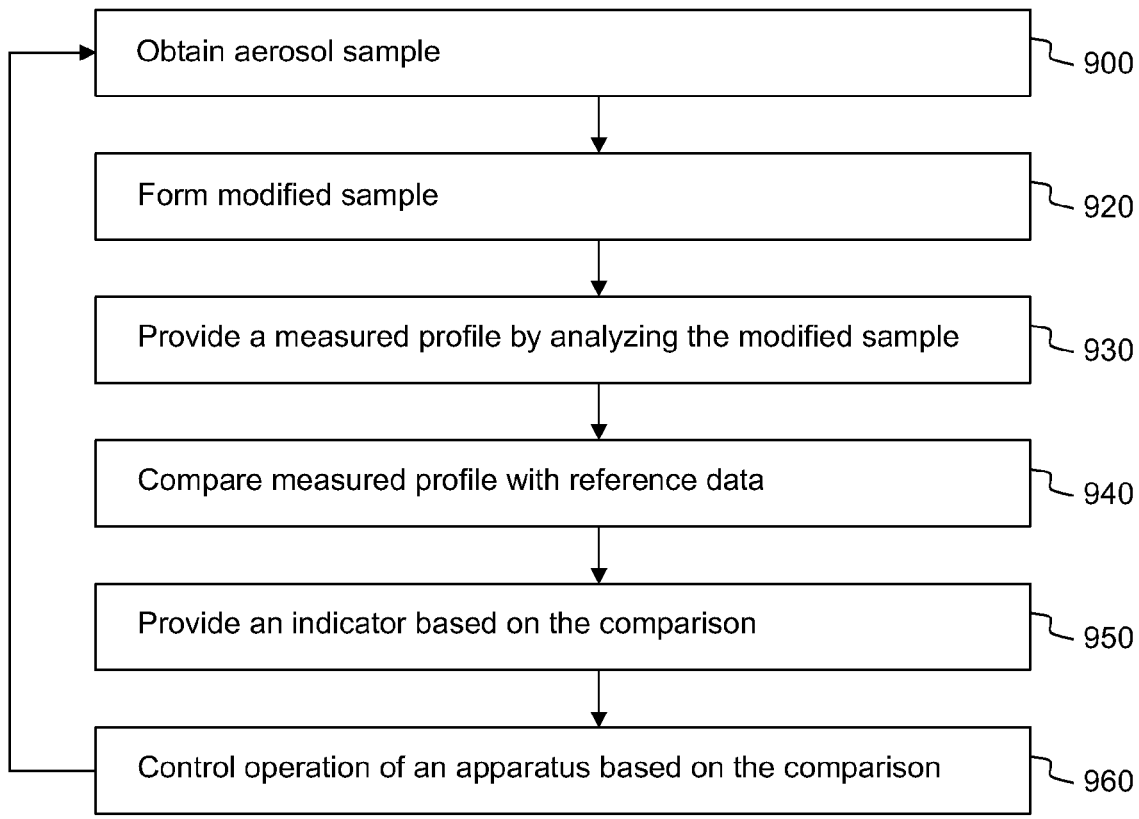
FIG. 9 shows, by way of example, method steps for controlling operation of a system.

FIG. 9 shows, by way of example, method steps for controlling operation of an apparatus or system based on analysis of the aerosol sample FG1. The aerosol sample FG1 may be obtained (step 900). The modified sample MG1 may be formed by using the electric field EF1 to separate the charged particles P2 from the gas phase of the modified sample MG1 (step 920). One or more profiles PRF may be provided by analyzing the gas phase of the modified sample MG1 (step 930). One or more profiles PRF may be compared with reference data REFDATA1 (step 940). An indicator IND1 may be provided based on the comparison (step 950). The indicator IND1 may indicate e.g. a composition of a material. Operation of an apparatus or a system may be controlled based on the comparison (960). A system 500 may be arranged to carry out the method steps of FIG. 9.

Figure 10A:
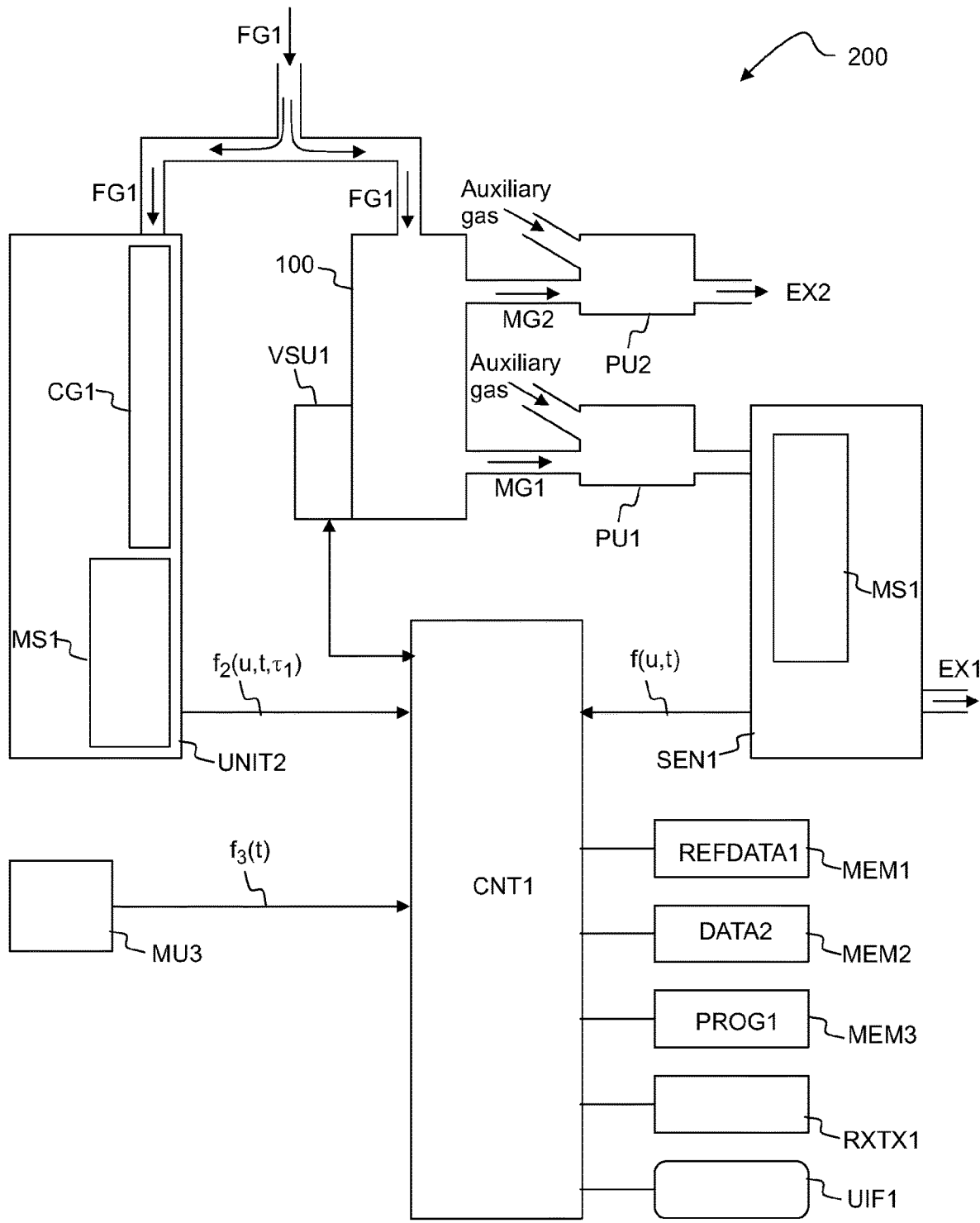
FIG. 10a shows, by way of example, a measuring apparatus comprising an auxiliary measuring unit.

Referring to FIG. 10a, the apparatus 200 may comprise one or more auxiliary measuring units UNIT2, in addition to the sensor unit SEN1. An auxiliary measuring unit UNIT2 may comprise e.g. a gas chromatograph column CG1 and a mass spectrometer MS1 connected in series. The auxiliary measuring unit UNIT2 may comprise e.g. a gas chromatograph column CG1 and a mobility spectrometer MS1 connected in series. The auxiliary measuring unit UNIT2 may optionally comprise a chromatograph column CG1 to provide additional selectivity. A part of the aerosol sample FG1 or an auxiliary sample obtained from the material MAT1 may be injected to the chromatograph column CG1 as a sample pulse, wherein gas VOC1 transmitted through the column may be guided to the mobility spectrometer and/or to the mass spectrometer for more detailed analysis. The auxiliary measuring unit UNIT2 may be arranged to provide auxiliary measured data, e.g. $f_2(u,t,\tau)$. The auxiliary measured data, e.g. $f_2(u,t,\tau)$ may be utilized in addition to the data f(u,t) obtained from the sensor unit SEN1. The auxiliary measured data, e.g. $f_2(u,t,\tau)$ may be used e.g. for improving the reliability of identifying a material MAT1 and/or for improving the accuracy of analysis of the material MAT1. The auxiliary measured data, e.g. $f_2(u,t,\tau)$ may be used e.g. for selecting one or more parameter values for an analysis algorithm, which identifies one or more materials based on analyzing the data f(u,t) obtained from the sensor unit SEN1. The auxiliary measured data, e.g. $f_2(u,t,\tau)$ may be used e.g. for selecting one or more relevant spectral features of the data f(u,t).

A chromatograph column CG1 may cause an additional time delay between sampling and detection. The additional time delay may be substantially avoided if the measurement is performed without using the chromatograph column CG1. The flow MG1 obtained from the modifier unit 100 may be guided to a mobility spectrometer MS1 or mass spectrometer MS1 such that the flow MG1 is not guided through a chromatograph column CG1.

The sensor unit SEN1 may provide measured data f(u,t) with a shorter time delay, and the auxiliary measuring unit UNIT2 may provide measured data $f_2(u,t,\tau)$ with a longer time delay.

In an embodiment, the sensor unit SEN1 may also comprise a chromatograph column CG1 for providing additional selectivity. The apparatus 200 may comprise one or more valves for bypassing the chromatograph column CG1 of the sensor unit SEN1, in order to avoid the time delay, if desired.

The apparatus 200 may comprise two or more sensor units SEN1, which may be used in parallel after the modifier unit 100. The sample MG1 may be distributed to two or more sensor units. A first sensor unit may be implemented such that it does not comprise a chromatograph column CG1. A second sensor unit may be implemented such that it comprises a chromatograph column CG1. The second sensor unit may comprise a chromatograph column CG1 connected in series with a mobility spectrometer MS1. The second sensor unit may comprise a chromatograph column connected in series with a mass spectrometer MS1.

The apparatus 200 and/or the measurement system 500 may comprise a monitoring unit MU3 for monitoring one or more sampling parameters. For example, the monitoring unit MU3 may be arranged to detect whether the inlet 301 of a sampling probe is in the vicinity of a material. The monitoring unit MU3 may comprise e.g. an antenna, an optical sensor, an electromechanical sensor for detecting proximity. The monitoring unit MU3 may comprise e.g. one or more electrodes for detecting impedance of a tissue. The apparatus 200 may be arranged to control operation of the apparatus based on a detected proximity of a material. The monitoring unit MU3 may comprise an optical sensor for measuring the color of the material MAT1. The measured color may be used as auxiliary information for improving the reliability of identifying a material MAT1 and/or for improving the accuracy of analysis of the material MAT1. The monitoring unit MU3 may comprise one or more electrodes and/or antennas for measuring an impedance of the material MAT1. The measured impedance may be used as auxiliary information for improving the reliability of identifying a material MAT1 and/or for improving the accuracy of analysis of the material MAT1. The monitoring unit MU3 may be arranged to provide auxiliary measured data, e.g. $f_3(t)$. The auxiliary measured data, e.g. $f_3(t)$ may be utilized in addition to the data f(u,t) obtained from the sensor unit SEN1. The auxiliary measured data, e.g. $f_3(t)$ may be used e.g. for improving the reliability of identifying a material MAT1 and/or for improving the accuracy of analysis of the material MAT1.

Figure 10B:
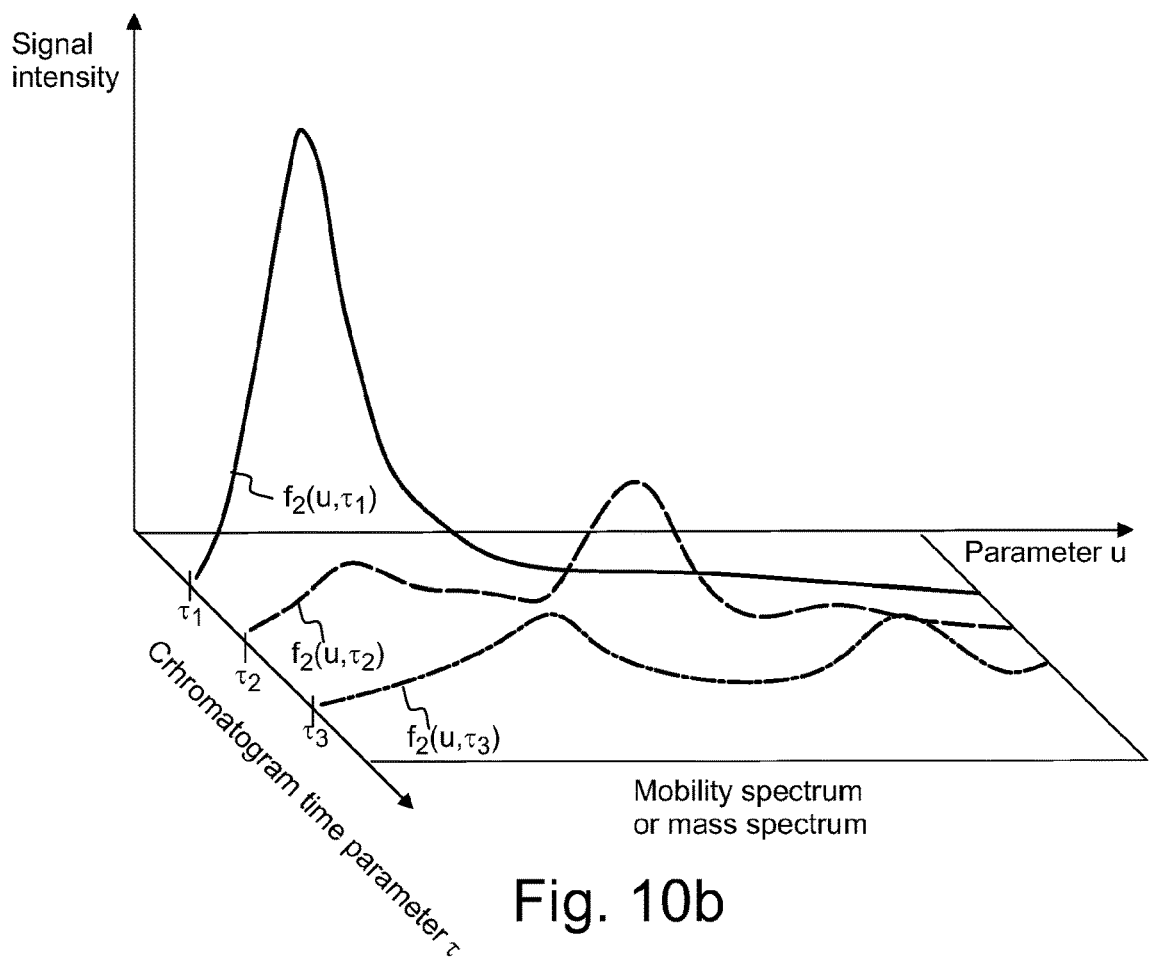
FIG. 10b shows, by way of example, multidimensional auxiliary spectral data measured by using the auxiliary measuring unit.

FIG. 10b shows, by way of example, a group of spectral profiles $f_2(u,\tau_1)$, $f_2(u,\tau_2)$, $f_2(u,\tau_3)$ measured by using a spectrometer MS1 connected in series with a chromatograph column CG1. The spectra $f_2(u,\tau_1)$, $f_2(u,\tau_2)$, $f_2(u,\tau_3)$ may represent a sample, which is injected to the chromatograph column CG1 e.g. at a time $t_k$. The spectra $f_2(u,\tau_1)$, $f_2(u,\tau_2)$, $f_2(u,\tau_3)$ may represent the same batch injected to the column CG1 at the time $t_k$. A first spectral profile $f_2(u,\tau_1)$ may be measured by the spectrometer MS1 at a time $t_{+\tau_1}$. A second spectral profile $f_2(u,\tau_2)$ may be measured by the spectrometer MS1 at a time $t_{+\tau_2}$. A third spectral profile $f_2(u,\tau_3)$ may be measured by the spectrometer MS1 at a time $t_{+\tau_3}$. The spectra $f_2(u,\tau_1)$, $f_2(u,\tau_2)$, $f_2(u,\tau_3)$ may be used as multidimensional auxiliary data $f_2(u,t,\tau)$ e.g. for improving the reliability of identifying a material MAT1 and/or for improving the accuracy of analysis of the material MAT1.

Figure 11:
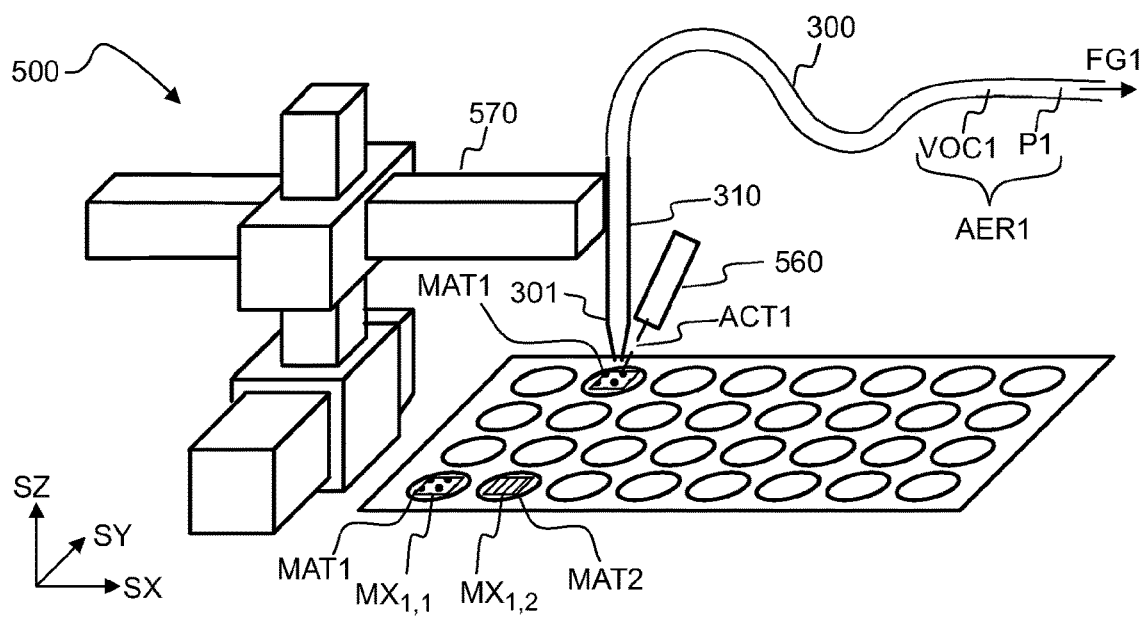
FIG. 11 shows, by way of example, in a three-dimensional view, an arrangement for analysis of multiple samples.

Referring to FIG. 11, the measurement system 500 may comprise an actuator 570 for changing the position of the inlet 301 of a sampling probe 310 with respect to an array of sample sites $MX_{1,1}$, $MX_{1,2}$, . . . . The actuator may move the probe 310 and/or the sample sites $MX_{1,1}$, $MX_{1,2}$, . . . . One or more sites $MX_{1,1}$, $MX_{1,2}$, . . . may carry and/or support sample material or materials MAT1, MAT2. For example, the system 500 may comprise a plate, which comprises a plurality of recessed portions $MX_{1,1}$, $MX_{1,2}$, . . . for supporting sample materials. The sample materials may be e.g. pieces of tissue, which have been separated from a body at an earlier stage. The system 500 may be arranged to identify and/or analyze the materials supported on the sites $MX_{1,1}$, $MX_{1,2}$, . . . . The apparatus 500 may comprise a processing unit 560 to cause emission of the aerosol AER1. The aerosol AER1 may be guided to the measuring apparatus 200 e.g. via a sampling line 300. The material may be processed e.g. by a laser beam and/or by heating. Some materials may also emit aerosol AER1 without processing.

The measurement system 500 may optionally comprise one or more valves for cleaning one or more parts of the system 500 with pure particle-free gas. One or more parts may be temporarily flushed with pure particle-free gas. The cleaning may be performed e.g. at regular intervals and/or when needed.

The pure cleaning gas may be e.g. nitrogen or filtered air. The pure cleaning gas may be obtained e.g. from a gas cylinder or by filtering ambient air. The cleaning gas may be provided such that the concentration of volatile organic compounds in the cleaning gas is zero or negligible. The concentration of volatile organic compounds in the cleaning gas may be below a predetermined limit.

Various aspects are illustrated by the following examples:

Example 1. An apparatus (200), comprising:
an input (201) to receive an aerosol sample (FG1),
a modifier unit (100) to provide a modified sample (MG1) by removing particles (P1) of the aerosol sample (FG1),
a sensor unit (SEN1) to measure one or more profiles (f(u)) by detecting molecules of the modified sample (MG1),
wherein the modifier unit (100) is arranged to generate a corona discharge (DSR1), to form charged particles (P2) by charging particles (P1) of the aerosol sample (FG1) with the corona discharge (DSR1), and to provide the modified sample (MG1) by removing the charged particles (P2).

Example 2. The apparatus (200) of example 1, wherein the modifier unit (100) is arranged to generate active species ($O_3$,$NO_X$) with the corona discharge (DSR1), and wherein the modifier unit (100) is arranged to provide the modified sample (MG1) by mixing the active species ($O_3$,$NO_X$) with the aerosol sample (FG1).

Example 3. The apparatus (200) of example 1 or 2, wherein the sensor unit (SEN1) comprises an ion mobility spectrometer (MS1) arranged to detect molecules of the modified sample (MG1).

Example 4. The apparatus (200) according to any of the examples 1 to 3, wherein the modifier unit (100) is arranged to generate the corona discharge (DSR1) with a corona electrode (ELEC1), the modifier unit (100) comprises a counter-electrode (ELEC2) for generating an electric field (EF1), the modifier unit (100) is arranged to form a first partial flow (MG1) and a second partial flow (MG2) from the aerosol sample flow (FG1) by deflecting the charged particles (P2) with the electric field (EF1) from the first partial flow (FG1) to the second partial flow (MG2), and wherein the modifier unit (100) comprises a flow divider (120) to separate the first partial flow (MG1) from the second partial flow (MG2).

Example 5. The apparatus (200) according to any of the examples 1 to 4, comprising at least one data processor (CNT1) configured to:
compare one or more measured profiles (f(u)) with reference data (REFDATA1), and
identify one or more substances (MAT1) based on the comparison.

Example 6. The apparatus (200) according to any of the examples 1 to 5, comprising a user interface (UIF1) to provide an indicator (IND1) indicative of an identified substance (MAT1).

Example 7. A system (500) comprising:
a surgical instrument (550), and
the apparatus (200) according to any of the examples 1 to 6.

Example 8. The system (500) of example 7, wherein the system (500) is arranged to control operation of the surgical instrument (550) based on the comparison.

Example 9. A method, comprising:
receiving an aerosol sample (FG1),
generating a corona discharge (DSR1),
converting particles (P1) of the aerosol sample (FG1) into charged particles (P2) by using the corona discharge (DSR1),
providing a modified sample (MG1) by removing charged particles (P2), and
measuring one or more profiles (f(u)) by detecting molecules of the modified sample (MG1).

Example 10. The method of example 9 comprising generating active species ($O_3$,$NO_X$) with the corona discharge (DSR1), and providing the modified sample (MG1) by mixing the active species ($O_3$,$NO_X$) with the aerosol sample (FG1).

Example 11. The method of example 9 or 10, comprising forming one or more measured profiles ((f(u)) by using an ion mobility spectrometer (MS1).

Example 12. The method according to any of the examples 9 to 11, comprising identifying one or more substances (MAT1) by comparing one or more measured profiles (f(u)) with reference data (REFDATA1).

Example 13. The method according to any of the examples 9 to 12 comprising providing an indicator (IND1) indicative of an identified substance (MAT1).

For the person skilled in the art, it will be clear that modifications and variations of the devices and the methods according to the present invention are perceivable. The figures are schematic. The particular embodiments described above with reference to the accompanying drawings are illustrative only and not meant to limit the scope of the invention, which is defined by the appended claims.

The invention claimed is:

1. An apparatus, comprising:
an input to receive an aerosol sample flow,
a modifier unit to provide a modified sample flow by removing particles of the aerosol sample flow, and
a sensor unit to measure a spectral profile by detecting molecules of the gas phase of the modified sample flow,
wherein the spectral profile is a mobility spectrum or a mass spectrometer spectrum, the modifier unit is arranged to generate a corona discharge with a corona electrode, to form charged particles by charging particles of the aerosol sample flow with the corona discharge, to generate chemically active species by guiding at least a part of the aerosol sample flow via the corona discharge, and to provide the modified sample flow by mixing the chemically active species with the aerosol sample flow and by removing the charged particles with an electric field, the particle removal efficiency of the modifier unit has a cutoff size to prevent propagation of particles larger than the cutoff size to the sensor unit, wherein the chemically active species include species selected from the group consisting of ozone and nitrogen oxides, wherein the modifier unit comprises a counter-electrode for generating the electric field, the modifier unit is arranged to form the modified sample flow and a second partial flow from the aerosol sample flow by deflecting the charged particles with the electric field from the modified sample flow to the second partial flow, and wherein the modifier unit comprises a flow divider to separate the modified sample flow from the second partial flow and also from the deflected particles carried in the second partial flow, and wherein the modifier unit comprises a first outlet to guide the modified sample flow out from the modifier unit, and wherein the modifier unit comprises a second outlet to guide the second partial flow out from the modifier unit.

2. The apparatus of claim 1, wherein the strength of the electric field has been selected such that the cutoff size is in the range of 1 nm to 20 nm.

3. The apparatus of claim 1, wherein the sensor unit comprises an ion mobility spectrometer arranged to detect molecules of the modified sample flow.

4. The apparatus claim 1, comprising at least one data processor configured to:
compare one or more measured spectral profiles with reference data, and
identify one or more substances based on the comparison.

5. The apparatus of claim 4, comprising a user interface to provide an indicator based on the comparison, the indicator being indicative of the composition or type of an identified substance.

6. A system comprising:
a surgical instrument, and
a measuring apparatus,
the measuring apparatus comprising:
an input to receive an aerosol sample flow,
a modifier unit to provide a modified sample flow by removing particles of the aerosol sample flow, and
a sensor unit to measure a spectral profile by detecting molecules of the gas phase of the modified sample flow,
wherein the spectral profile is a mobility spectrum or a mass spectrometer spectrum, the modifier unit is arranged to generate a corona discharge with a corona electrode, to form charged particles by charging particles of the aerosol sample flow with the corona discharge, to generate chemically active species by guiding at least a part of the aerosol sample flow via the corona discharge, and to provide the modified sample flow by mixing the chemically active species with the aerosol sample flow and by removing the charged particles with an electric field, wherein the chemically active species include species selected from the group consisting of ozone and nitrogen oxides, wherein the particle removal efficiency of the modifier unit has a cutoff size to prevent propagation of particles larger than the cutoff size to the sensor unit, wherein the modifier unit comprises a counter-electrode for generating the electric field, the modifier unit is arranged to form the modified sample flow and a second partial flow from the aerosol sample flow by deflecting the charged particles with the electric field from the modified sample flow to the second partial flow, and wherein the modifier unit comprises a flow divider to separate the modified sample flow from the second partial flow and also from the deflected particles carried in the second partial flow, and wherein the modifier unit comprises a first outlet to guide the modified sample flow out from the modifier unit, and wherein the modifier unit comprises a second outlet to guide the second partial flow out from the modifier unit.

7. A method, comprising:
receiving an aerosol sample flow,
generating a corona discharge with a corona electrode,
converting particles of the aerosol sample flow into charged particles in a modifier unit by using the corona discharge,
generating chemically active species with the corona discharge by guiding at least a part of the aerosol sample flow via the corona discharge, providing a modified sample flow by mixing the chemically active species with the aerosol sample flow and by removing the charged particles with an electric field in the modifier unit, and measuring a mobility spectrum and/or a mass spectrum in a sensor unit by detecting molecules of the gas phase of the modified sample flow, wherein the chemically active species include species selected from the group consisting of ozone and nitrogen oxides, wherein the particle removal efficiency of the modifier unit has a cutoff size to prevent propagation of particles larger than the cutoff size to the sensor unit, wherein the modifier unit comprises a counter-electrode for generating the electric field, the modifier unit is arranged to form the modified sample flow and a second partial flow from the aerosol sample flow by deflecting the charged particles with the electric field from the modified sample flow to the second partial flow, and wherein the modifier unit comprises a flow divider to separate the modified sample flow from the second partial flow and also from the deflected particles carried in the second partial flow; and wherein the method further comprises:

guiding the modified sample flow via a first outlet, and guiding the second partial flow via a second outlet.

8. The method of claim 7, wherein the strength of the electric field is selected such that the cutoff size is in the range of 1 nm to 20 nm.

9. The method of claim 7, comprising forming one or more measured profiles by using an ion mobility spectrometer.

10. The method of claim 7, comprising identifying one or more substances by comparing one or more measured spectral profiles with reference data.

11. The method of claim 10, comprising providing an indicator based on the comparison, the indicator being indicative of the composition or type of an identified substance.

* * * * *